(12) United States Patent
Archer et al.

(10) Patent No.: US 8,852,550 B2
(45) Date of Patent: Oct. 7, 2014

(54) CHELATOR CONJUGATES

(75) Inventors: Colin Mill Archer, Buckinghamshire (GB); Harry John Wadsworth, Buckinghamshire (GB); Torgrim Engell, Oslo (NO)

(73) Assignee: GE Healthcare Limited, Buckinghamshire (GB)

( * ) Notice: Subject to any disclaimer, the term of this patent is extended or adjusted under 35 U.S.C. 154(b) by 297 days.

(21) Appl. No.: 12/571,508

(22) Filed: Oct. 1, 2009

(65) Prior Publication Data

US 2010/0040542 A1 Feb. 18, 2010

Related U.S. Application Data

(62) Division of application No. 10/483,455, filed as application No. PCT/GB02/03168 on Jul. 10, 2002, now Pat. No. 7,597,875.

(30) Foreign Application Priority Data

Jul. 20, 2001 (GB) .................. 0116815.2

(51) Int. Cl.
| | |
|---|---|
| *A61K 51/00* | (2006.01) |
| *A61M 36/14* | (2006.01) |
| *A61K 49/00* | (2006.01) |
| *C07K 14/745* | (2006.01) |
| *C07K 7/06* | (2006.01) |
| *A61K 47/48* | (2006.01) |
| *A61K 51/08* | (2006.01) |
| *A61K 38/00* | (2006.01) |

(52) U.S. Cl.
CPC .............. *C07K 7/06* (2013.01); *A61K 49/0002* (2013.01); *C07K 14/745* (2013.01); *A61K 38/00* (2013.01); *A61K 47/48276* (2013.01); *A61K 51/088* (2013.01); *A61K 47/48215* (2013.01)
USPC ........................................ 424/1.37; 424/1.65

(58) Field of Classification Search
USPC ......................................................... 424/1.65
See application file for complete search history.

(56) References Cited

U.S. PATENT DOCUMENTS

| | | | |
|---|---|---|---|
| 4,268,547 A | 5/1981 | Backhouse | |
| 5,302,370 A | 4/1994 | Neumeier et al. | |
| 5,688,487 A | 11/1997 | Linder et al. | |
| 5,705,143 A | 1/1998 | Bower et al. | |
| 5,997,843 A | 12/1999 | Archer et al. | |
| 6,660,246 B1 | 12/2003 | Nowotnik et al. | |
| 6,783,711 B2 * | 8/2004 | Kurth et al. .................... 264/41 |
| 6,988,794 B2 | 1/2006 | Arase et al. | |

FOREIGN PATENT DOCUMENTS

WO 9960018 11/1999

* cited by examiner

*Primary Examiner* — Michael G Hartley
*Assistant Examiner* — Melissa Perreira
(74) *Attorney, Agent, or Firm* — Yonggang Ji

(57) ABSTRACT

The present invention relates to improved chelator conjugates with biological targeting molecules, suitable for forming metal complexes with radiometals. The radiometal complexes, especially with the radiometal $^{99m}$Tc, are useful as radiopharmaceuticals.

25 Claims, 3 Drawing Sheets

Figure 1: Chemical Structures of Compounds 1 to 6.
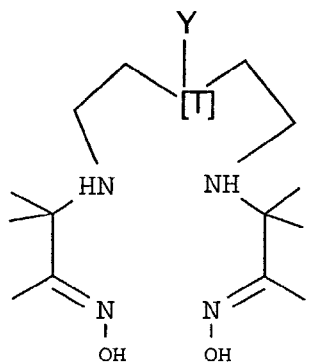
| Compound | T | Y |
|---|---|---|
| 1 | CH | -CH$_2$CH$_2$NH$_2$ |
| 2 | CH | -CH$_2$CH$_2$NH(CO)C$_6$H$_5$ |
| 3 | N | -CH$_2$CH$_2$NH(CO)C$_6$H$_5$ |
| 4 | CH | -CH$_2$CH$_2$NH(CO)(CH$_2$)$_3$CO$_2$H |
| 5 | CH | -GKLLT(3-I)YPSVQEQN-Ac |
| 6 | N | -GKLLT(3-I)YPSVQEQN-Ac |
Figure 2: Chemical Structure of Compound 5 – The Peptide-chelator Conjugate Ac-Asn-Gln-Glu-Gln-Val-Ser-Pro-(I-Tyr)-Thr-Leu-Leu-Lys-Gly-[Compound 1].
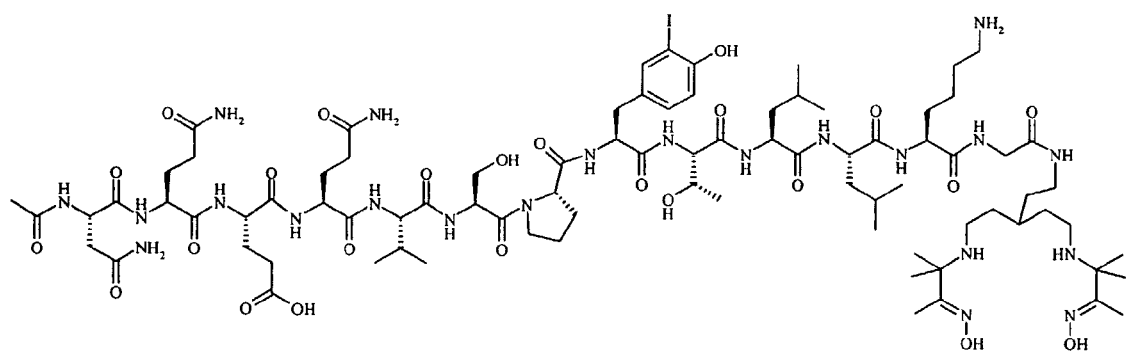

Figure 3: Azide Route to 1,1,1-*tris*(2-aminoethyl)methane.
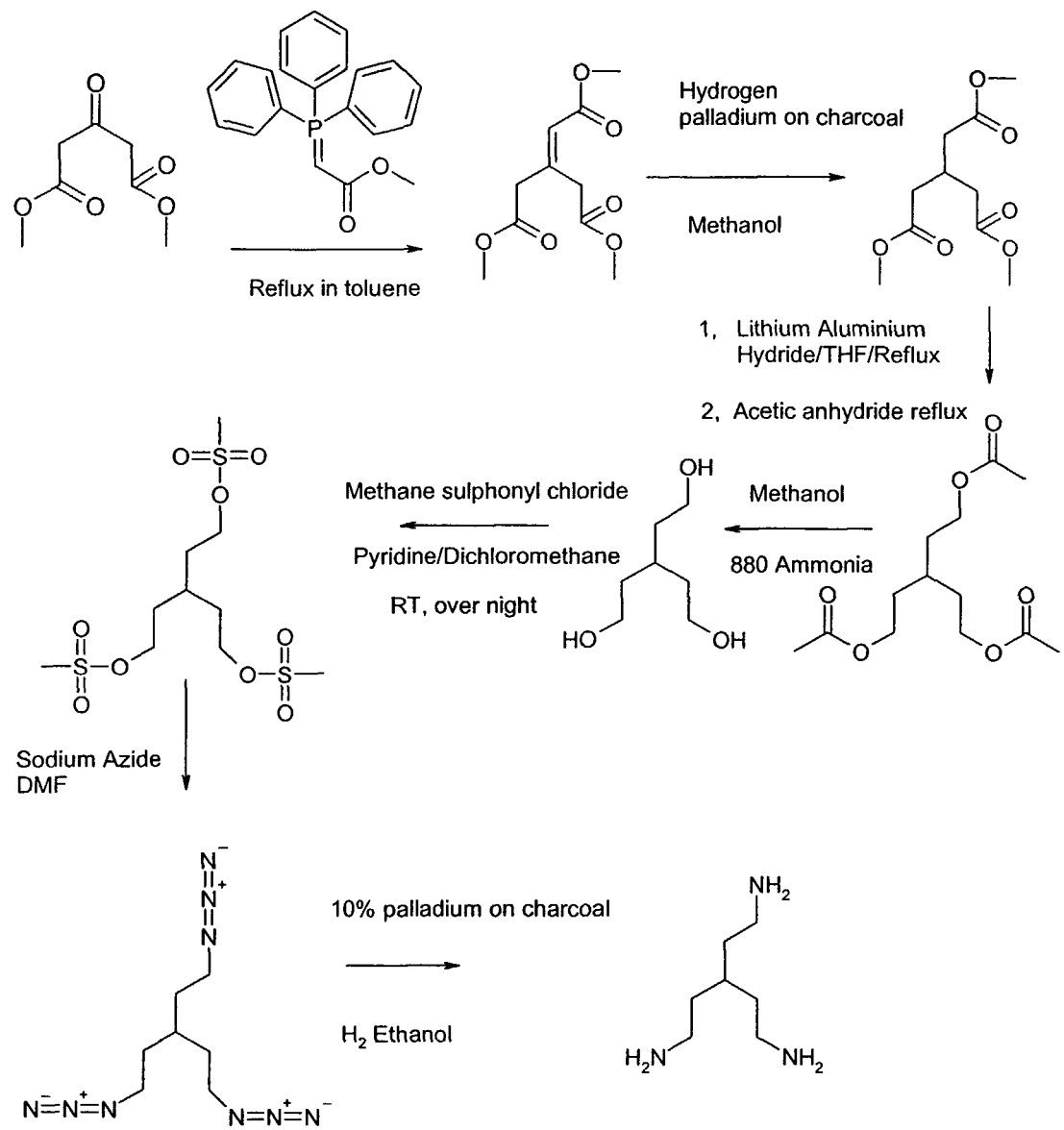

Figure 4: Alternative Synthesis of 1,1,1-*tris*(2-aminoethyl)methane.
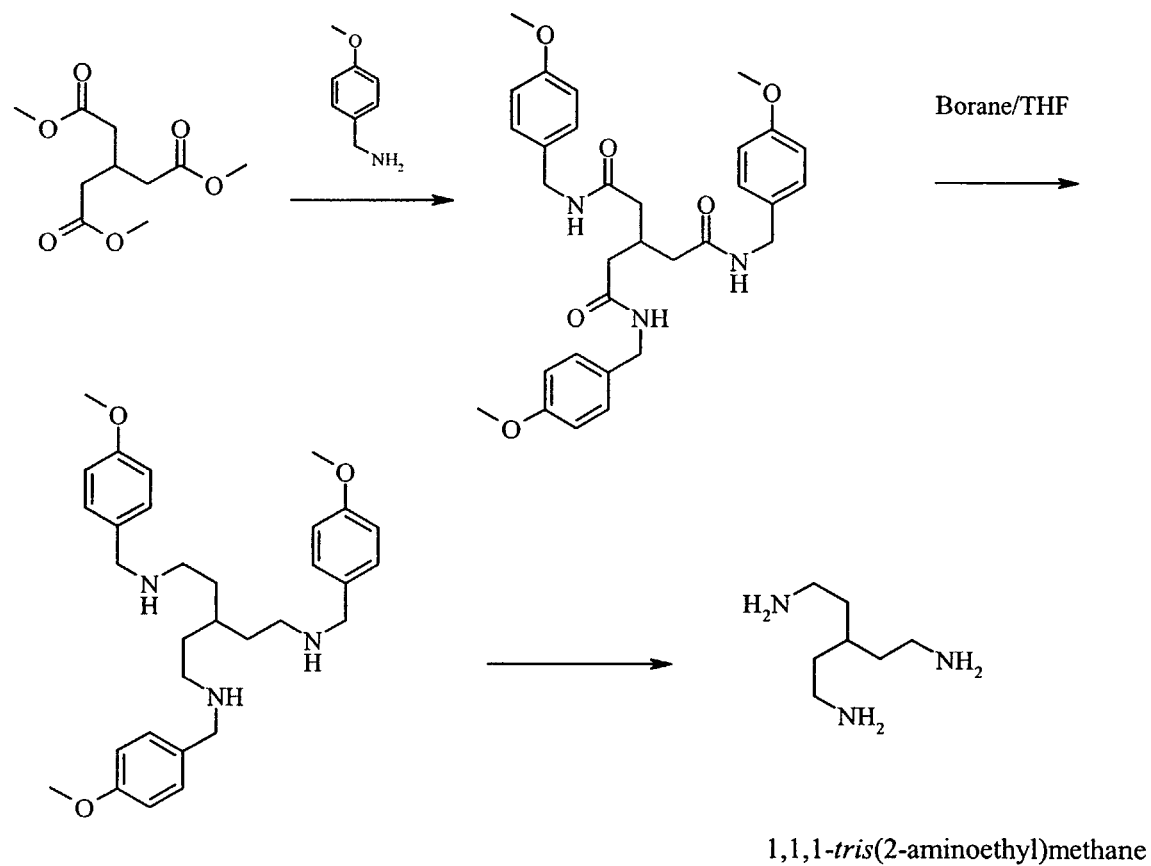
1,1,1-*tris*(2-aminoethyl)methane

CHELATOR CONJUGATES

This application is a divisional of U.S. application Ser. No. 10/483,455 filed Jun. 21, 2004 which is a filing under 35 U.S.C. 371 of international application number PCT/GB02/003168, filed Jul. 10, 2002, which claims priority to application number 0116815.2 filed Jul. 20, 2001, in Great Britain the entire disclosure of which is hereby incorporated by reference.

FIELD OF THE INVENTION

The present invention relates to improved chelator conjugates with biological targeting molecules, suitable for forming metal complexes with radiometals. The radiometal complexes are useful as radiopharmaceuticals, especially with $^{99m}$Tc.

BACKGROUND TO THE INVENTION

Diaminedioximes are a known class of chelating agents, which have been shown to form

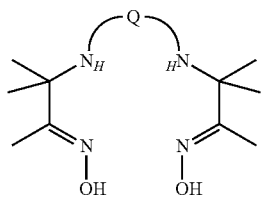

Q=—(CH$_2$)$_3$— ie. propyleneamine oxime or PnAO;
Q=—(CH$_2$)$_4$— ie. butyleneamine oxime or BnAO;
Q=—(CH$_2$)$_5$— ie. pentyleneamine oxime or PentAO;
complexes with the radiometal $^{99m}$Tc.

The ligand PentAO was first disclosed by S. Jurisson et al [Inorg. Chem., 26, 3576-82 (1987)], who showed that its' metal complex with the long-lived radiometal $^{99}$Tc was neutral, with a Tc(V) dioxo core (ie. TcO$_2^+$). J-M Lo et al [Appl. Rad. Inst, 44, 1139-46 (1993)] described the synthesis of PentAO and it's complexation with $^{99m}$Tc.

U.S. Pat. No. 5,688,487 discloses chelate-conjugates of diaminedioximes having a C$_{2-5}$ alkylene bridge with nitroimidazole biological targeting molecules, for hypoxia imaging. Conjugation of the nitroimidazole at the C1 (oxime methyl) position is described.

WO 95/04552 discloses nitroimidazole conjugates of BnAO and PentAO. The Example shows conjugation at the C1 (oxime methyl) position.

WO 95/19187 discloses conjugates of linear or cyclic 3-50 mer synthetic peptides with polydentate chelating agents attached at the peptide carboxyl terminus, for use as radiopharmaceuticals. Diaminedioximes such as PnAO, BnAO and PentAO are described as suitable chelating agents.

WO 99/60018 discloses diaminedioxime chelate conjugates of diaminedioxime ligands with peptides for thrombus imaging. A preferred such chelator is said to be a diaminedioxime with Q=—(CH$_2$)$_2$NR(CH$_2$)$_2$—.

THE PRESENT INVENTION

The diaminedioxime-peptide chelator conjugates of WO 99/60018 of Formula I:

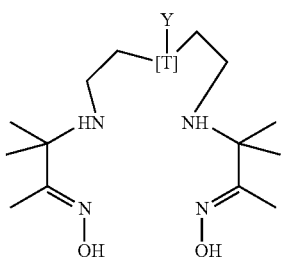

Formula I where T=N and Y=—CH$_2$CH$_2$NH— [peptide], do, however, suffer from significant disadvantages. Thus, on chelation with $^{99m}$Tc, this aza-diaminedioxime forms several technetium species, which can be separated and detected by chromatography. At ambient temperature, the initial radiolabelled species (intermediates) are converted over time (2-3 hrs) to a stable product. This intermediate-product conversion can be promoted by the use of higher pH (>pH 8) and heating. These conditions are not ideal in a hospital radiopharmacy, therefore a chelator with fewer intermediates and/or a faster intermediate-product conversion rate is desirable. Clearly, the need for heating and possibly relatively high pH to achieve adequate radiochemical purity (RCP) of the desired $^{99m}$Tc species is undesirable, since such heating may degrade the attached biological targeting molecule or peptide. A further problem with the aza-diaminedioxime chelators of Formula I is that the tertiary amine nitrogen of the bridgehead position is relatively basic. This means that, on formation of the corresponding $^{99m}$Tc complex in aqueous solution, the tertiary amine is at least partially protonated, with the result that the conjugate is charged. This charge may limit the applications of the labelled biological targeting moiety, since the charge may make it more difficult for the radiolabelled conjugate to cross cell membranes.

The present invention provides an alternative chelator system (Formula I where T=C), which overcomes these prior art problems, and provides conjugates which can be radiolabelled to give good RCP at room temperature, under aqueous conditions at near neutral pH. The radiometal complexes are of good stability. Prior art N2S2 and N3S thiol-containing bifunctional chelators suffer from the disadvantage that the thiols are air sensitive, rapidly oxidising in air to the corresponding disulphides under neutral to basic conditions. They must therefore be kept in an inert atmosphere before use or in a protective matrix. Alternatively they can be used as protected species such as thioacetate, or a tetrahydropyranyl hemithioketal, but this necessitates removal of protecting groups before use with acid or base and heating. All these features reduce the convenience of these chelators compared to the chelators of the present invention. Hence, the present chelators are useful for the conjugation and radiolabelling of a wide range of biological targeting moieties.

DETAILED DESCRIPTION OF THE INVENTION

In a first aspect, the present invention provides, a chelator conjugate of a diaminedioxime ligand with a biological targeting moiety. The term "chelator conjugate" means a compound where a metal chelating agent is covalently linked ('conjugated') to a biological targeting moiety. The chelator conjugate is of Formula II:

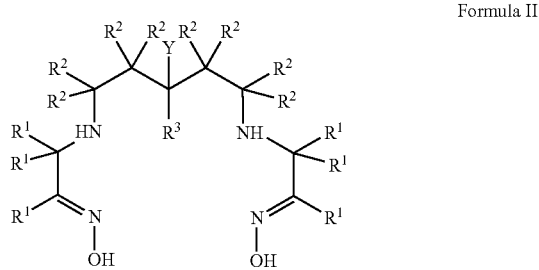

Formula II where:
each $R^1$, $R^2$ and $R^3$ is independently an R group;
Y is $-(A)_n-X-Z$
where: X is $-NR^4-$, $-CO_2-$, $-N(C=S)-$, $-N(C=O)-$, $-S-$ or $-O-$;
Z is a biological targeting moiety,
$R^4$ is independently an R group;
$-(A)_n-$ is a linker group where each A is independently $-CR_2-$, $-CR=CR-$, $-C\equiv C-$, $-NRCO-$, $-CONR-$, $-SO_2NR-$, $-NRSO_2-$, $-CR_2OCR_2-$, $-CR_2SCR_2-$, $-CR_2NRCR_2-$, a $C_{4-8}$ cycloheteroalkylene group, a $C_{4-8}$ cycloalkylene group, a $C_{5-12}$ arylene group, a $C_{3-12}$ heteroarylene group or a polyalkyleneglycol, polylactic acid or polyglycolic acid moiety;
n is an integer of value 0 to 10;
each R group is independently H or $C_{1-10}$ alkyl, $C_{3-10}$ alkylaryl, $C_{2-10}$ alkoxyalkyl, $C_{1-10}$ hydroxyalkyl, $C_{1-10}$ fluoroalkyl or 2 or more R groups, together with the atoms to which they are attached form a carbocyclic, heterocyclic, saturated or unsaturated ring.

By the term "biological targeting moiety" is meant: 3-100 mer peptides or peptide analogues which may be linear peptides or cyclic peptides or combinations thereof; monoclonal antibodies or fragments thereof; or enzyme substrates or inhibitors; synthetic receptor-binding compounds; oligonucleotides, or oligo-DNA or oligo-RNA fragments. The biological targeting moiety may be of synthetic or natural origin, but is preferably synthetic. Preferred biological targeting moieties are 3-20 mer peptides, which may be of synthetic or natural origin, but are preferably synthetic. By the term "cyclic peptide" is meant a sequence of 5 to 15 amino acids in which the two terminal amino acids are bonded together by a covalent bond which may be a peptide or disulphide bond or a synthetic non-peptide bond such as a thioether, phosphodiester, disiloxane or urethane bond.

By the term "amino acid" is meant an L- or D-amino acid, amino acid analogue or amino acid mimetic which may be naturally occurring or of purely synthetic origin, and may be optically pure, i.e. a single enantiomer and hence chiral, or a mixture of enantiomers. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retro-inverso peptides, thioamides, cycloalkanes or 1,5-disubstituted tetrazoles [see M. Goodman, Biopolymers, 24, 137, (1985)].

Suitable peptides for use in the present invention include:
somatostatin, octreotide and analogues,
peptides which bind to the ST receptor, where ST refers to the heat-stable toxin produced by *E. coli* and other micro-organisms;
laminin fragments eg. YIGSR, PDSGR, IKVAV, LRE and KCQAGTFALRGDPQG,
N-formyl peptides for targeting sites of leucocyte accumulation,
Platelet factor 4 (PF4) and fragments thereof,
RGD-containing peptides,
peptide fragments of $\alpha_2$-antiplasmin, fibronectin or beta-casein, fibrinogen or thrombospondin. The amino acid sequences of $\alpha_2$-antiplasmin, fibronectin, beta-casein, fibrinogen and thrombospondin can be found in the following references: $\alpha_2$-antiplasmin precursor [M. Tone et al., J. Biochem, 102, 1033, (1987)]; beta-casein [L. Hansson et al, Gene, 139, 193, (1994)]; fibronectin [A. Gutman et al, FEBS Lett., 207, 145, (1996)]; thrombospondin-1 precursor [V. Dixit et al, Proc. Natl. Acad. Sci., USA, 83, 5449, (1986)]; R. F. Doolittle, Ann. Rev. Biochem., 53, 195, (1984).

Preferably the peptides of the present invention comprise an amino acid sequence is taken from the N-terminus of:
(i) $\alpha_2$-Antiplasmin,
i.e. NH$_2$-Asn-Gln-Glu-Gln-Val-Ser-Pro-Leu-Thr-Leu-Thr-Leu-Leu-Lys-OH or variants of this in which one or more amino acids have been exchanged, added or removed such as: NH$_2$-Asn-Gln-Glu-Gln-Val-Ser-Pro-Leu-Thr-Leu-Thr-Leu-Leu-Lys-Gly-OH, NH$_2$-Asn-Gln-Glu-Ala-Val-Ser-Pro-Leu-Thr-Leu-Thr-Leu-Leu-Lys-Gly-OH, NH$_2$-Asn-Gln-Glu-Gln-Val-Gly-OH; or
(ii) Casein
ie. Ac-Leu-Gly-Pro-Gly-Gln-Ser-Lys-Val-Ile-Gly.

Synthetic peptides of the present invention may be obtained by conventional solid phase synthesis, as described in P. Lloyd-Williams, F. Albericio and E. Girald; *Chemical Approaches to the Synthesis of Peptides and Proteins*, CRC Press, 1997.

Suitable monoclonal antibodies or fragments thereof for use in the present invention include: antibodies to the CD-20 antigen expressed on the surface of B-cells; anti-leucocyte or anti-granulocyte antibodies; anti-myosin antibodies or antibodies to carcinoembryonic antigen (CEA).

Suitable enzyme substrates or inhibitors include glucose and glucose analogues such as fluorodeoxyglucose; fatty acids or elastase inhibitors.

Suitable synthetic receptor-binding compounds include estradiol, estrogen, progestin, progesterone and other steroid hormones; ligands for the dopamine D-1 or D-2 receptor, or dopamine transporter such as tropanes; and ligands for the serotonin receptor.

By the term 'fluoroalkyl' is meant an alkyl group with at least one fluorine substituent, ie. the term encompasses groups from monofluoroalkyl (eg. $-CH_2F$) to perfluoroalkyl (eg. $CF_3$).

In the diaminedioxime chelators of the present invention, $R^3$ is preferably H. It is also preferred that at least one $R^2$ group is H, more preferably all the $R^2$ groups are H. Each $R^1$ is preferably $C_{1-3}$ alkyl, $C_{2-4}$ alkoxyalkyl, $C_{1-3}$ hydroxyalkyl, or $C_{1-3}$ fluoroalkyl, and is most preferably $C_{1-3}$ alkyl or $C_{1-3}$ fluoroalkyl. It is most especially preferred that all the $R^1$ groups are $CH_3$.

Preferred chelator conjugates of Formula II wherein 2 or more R groups which, together with the atoms to which they are attached, form a carbocyclic, heterocyclic, saturated or unsaturated ring, comprise such rings having 3- to 6-members, especially 5- or 6-members. Most preferred such rings are saturated carbocyclic rings. Preferred carbocyclic rings are those in which 2 $R^1$ groups attached to either the same or adjacent carbon atoms are combined to form 3- to 6-membered, especially 5- or 6-membered saturated rings.

It is envisaged that the role of the linker group $-(A)_n$ is to distance the relatively bulky radiometal complex which results upon metal coordination, from the active site of the biological targeting moiety so that eg. receptor binding is not impaired. This can be achieved by a combination of flexibility (eg. simple alkyl chains), so that the bulky group has the freedom to position itself away from the active site and/or rigidity such as a cycloalkyl or aryl spacer which orientates the metal complex away from the active site. The nature of the linker group can also be used to modify the biodistribution of the resulting radiometal complex of the conjugate. Thus, eg. the introduction of ether groups in the linker will help to minimise plasma protein binding. Preferred linker groups $-(A)_n$ have a backbone chain of linked atoms which make up the $-(A)_n$ moiety contain 2 to 10 atoms, most preferably 2 to 5 atoms, with 2 or 3 atoms being especially preferred. A minimum linker group backbone chain of 2 atoms confers the advantage that the chelator is well-separated from the biological targeting moiety so that any interaction is minimised. A further advantage is that the potential chelate ring size of the X and Z groups is so large (at least 8 for a 2 atom backbone chain) that these groups are unlikely to compete effectively with the coordination of the chelator to a radiometal. In this way, both the biological targeting characteristics of the biological targeting moiety, and the metal complexing capability of the diaminedioxime chelator is maintained in conjugates of this type.

Non-peptide linker groups such as alkylene groups or arylene groups have the advantage that there are no significant hydrogen bonding interactions with the conjugated biological targeting moiety so that the linker does not wrap round onto the biological targeting moiety. Preferred alkylene spacer groups are $-(CH_2)_n-$ where n is 2 to 5. Preferred arylene spacers are of formula:

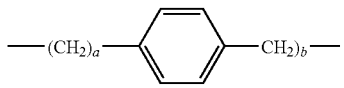

where: a and b are independently 0, 1 or 2.

A preferred Y group is thus $-CH_2CH_2-X-Z$, most preferably $-CH_2CH_2-NR^4-Z$, with $Y=-CH_2CH_2-NH-Z$ being especially preferred. This grouping has the additional advantage that it stems from the intermediate $R^3C(CH_2CH_2NH_2)_3$, preferably the intermediate $HC(CH_2CH_2NH_2)_3$, which being symmetrical are much easier to synthesise, since triamines having different chain lengths would require the use of synthetic strategies to chemically distinguish the various amines (eg. via protecting groups).

The group X is a functional group which permits facile conjugation of the chelating agent to the biological targeting moiety Z. Since most peptides and proteins have available carboxyl or amino sites for functionalisation, preferred X groups when Z is a peptide or protein are $-NR^4-$ and $-CO_2-$, since these permit facile conjugation via amide bonds. Cysteine-containing peptides and proteins may have free thiol groups, preferred X groups when Z is a cysteine-containing peptide or protein, are thiophilic groups such as maleimide and acrylamide, since these permit facile conjugation via thioether bonds.

Preferred diaminedioxime chelators of the present invention are symmetrical, ie. the two $-CR^2_2R^2_2NHCR^1_2C(=N-OH)R^1$ substituents on the $-CY(R^3)-$ moiety are chosen to be the same. This has the advantage that, the chelator does not contain a chiral centre, since such centres may generate diastereomeric radiometal complexes and possibly require the purification of particular isomers.

The chelator conjugates of Formula II may optionally be used in acid salt form, ie. where one or more amines of either the diaminedioxime donor set or the Y group are protonated with a biocompatible acid. Such salts may be obtained directly, eg. by HPLC purification employing such acids in the mobile phase (eg. acetic or trifluoroacetic acid), or by addition of the biocompatible acid to a solution of the chelator conjugate. The salt form may be useful to aid purification (eg. via precipitation or recrystallisation), or may facilitate dissolution in aqueous media (after which the pH can be readily adjusted if necessary).

The chelator conjugates of the present invention can be prepared by reaction of a bifunctional chelate of Formula III with the biological targeting moiety:

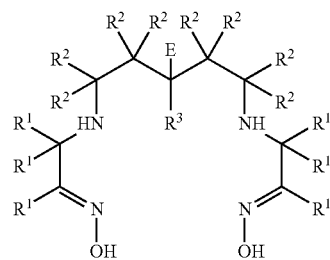

Formula III where:
each $R^1$, $R^2$ and $R^3$ is independently an R group;
E is $-(A)_n-J$
  where: J is a functional group suitable for conjugation to Z;
  $-(A)_n-$ is a linker group where each A is independently $-CR_2-$, $-CR=CR-$, $-C\equiv C-$, $-NRCO-$, $-CONR-$, $-SO_2NR-$, $-NRSO_2-$, $-CR_2OCR_2-$, $-CR_2SCR_2-$, $-CR_2NRCR_2-$, a $C_{4-8}$ cycloheteroalkylene group, a $C_{4-8}$ cycloalkylene group, a $C_{5-12}$ arylene group, a $C_{3-12}$ heteroarylene group or a polyalkyleneglycol, polylactic acid or polyglycolic acid moiety;
  n is an integer of value 0 to 10;
each R group is independently H or $C_{1-10}$ alkyl, $C_{3-10}$ alkylaryl, $C_{2-10}$ alkoxyalkyl, $C_{1-10}$ hydroxyalkyl, $C_{1-10}$ fluoroalkyl, or 2 or more R groups, together with the atoms to which they are attached form a carbocyclic, heterocyclic, saturated or unsaturated ring.

By the term "functional group suitable for conjugation" is meant a functional group which will react with a corresponding functional group of Z (typically an amine, carboxyl or thiol group) to chemically link the diaminedioxime chelator to Z. Preferred such functional groups suitable for conjugation are: $-NR^5R^6$, $-CO_2M$, $-NCS$, $-NCO$, $-SM^1$, $-OM^1$, maleimide or acrylamide, where $R^5$ and $R^6$ are independently an R group or $P^G$; M is H, a cation, $P^G$ or an active ester; $M^1$ is H or $P^G$; and $P^G$ is a protecting group. The cation is suitably a positively-charged counterion, such as a metal ion, ammonium ($NH_4^+$) or quaternary ammonium or phosphonium ion. Preferably, the cation is a biocompatible cation. The terms 'biocompatible cation', 'active ester' and 'protecting group' are as defined below. When the functional group is —$NR^5R^6$, at least one and preferably both of $R^5$ and $R^6$ is H.

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the group in question may be used to conjugate the bifunctional chelate of Formula III to the biological targeting moiety. Protecting groups are well known to those skilled in the art and are suitably chosen from, when J is —$NR^5R^6$: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl); and when J is —$CO_2P^G$: methyl ester, tert-butyl ester, benzyl ester when J is —$OP^G$, suitable protecting groups are: acetyl, benzoyl, trityl (Trt) or tetrabutyldimethylsilyl. When J is —$SP^G$, suitable protecting groups are: Trityl and 4-methoxy-benzyl. The use of further protecting groups are described in 'Protective Groups in Organic Synthesis', Theorodora W. Greene and Peter G. M. Wuts, (John Wiley & Sons, 1991).

By the term "biocompatible cation" is meant a positively charged counterion which forms a salt with an ionised, negatively charged group, where said positively charged counterion is also non-toxic and hence suitable for administration to the mammalian body, especially the human body. Examples of suitable biocompatible cations include: the alkali metals (eg. sodium or potassium); the alkaline earth metals (eg. calcium or magnesium); and the ammonium ion. A preferred biocompatible cation is sodium ion ($Na^+$).

By the term "active ester" is meant an ester derivative of the carboxylic acid which is designed to be a better leaving group, and hence permit more facile reaction with nucleophiles present on the biological targeting moiety such as amines. Examples of suitable active esters are: N-hydroxysuccinimide (NHS), pentafluorophenol, pentafluorothiophenol, para-nitrophenol and hydroxybenzotriazole.

Amine-functionalised chelators of Formula III (ie. J=—$NR^5R^6$) can thus be conjugated to the carboxyl group(s) of a biological targeting moiety, via amide bonds. This coupling can be carried out directly (eg. using solid phase peptide synthesis), or in the presence of a suitable activating agent, such as BOP [ie. benzotriazol-1-yloxy-tris(dimethylamino)-phosphonium] or N,N'-dicyclohexylcarbodiimide (DCCI). The coupling can also be carried out via appropriate intermediates as is known in the art, such as activated esters of the carboxyl group of the biological targeting moiety. Alternatively, the pendant amine group of the bifunctional chelator can first be converted to an isothiocyanate (—NCS) or isocyanate group (—NCO) group, which permit conjugation to amine-containing biological targeting moieties, via the formation of thiourea and urea linkages respectively. Alternatively, the pendant amine group of the bifunctional chelator can be reacted with a diacid to introduce a terminal carboxyl group via a linker group. A bifunctional chelator bearing a carboxyl function (ie. J=—$CO_2M$) can be used in a similar manner to couple directly to amine-containing biological targeting moieties via an amide bond. The bifunctional chelate may also bear a group designed to react with thiol groups on the biological targeting moiety to form stable thioether linkages. Examples of such groups are maleimides (which may be prepared by reaction of maleic anhydride with the corresponding amine, followed by heating with acetic anhydride), and acrylamides (which may be prepared by reaction of acrylyl chloride with the amine).

In a second aspect, the present invention provides radiometal complexes of the chelator conjugate described above. Suitable radiometals can be either positron emitters such as $^{64}Cu$, $^{48}V$, $^{52}Fe$, $^{55}Co$, $^{94m}Tc$ or $^{68}Ga$; or γ-emitters such as $^{99m}Tc$, $^{111}In$, $^{113m}In$ or $^{67}Ga$. Most preferred radiometals for diagnostic imaging are γ-emitters, especially $^{99m}Tc$. Metal complexes of certain radionuclides may be useful as radiopharmaceuticals for the radiotherapy of various diseases such as cancer or the treatment of thrombosis or restenosis. Useful radioisotopes for such radiotherapeutic applications include: $^{90}Y$, $^{89}Sr$, $^{67}Cu$, $^{103}Pd$, $^{186}Re$, $^{188}Re$, $^{169}Er$, $^{153}Sm$ and $^{198}Au$. It is strongly preferred that the biological targeting moiety Z is bound to the chelator in such a way that the linkage does not undergo facile metabolism in blood, which would result in the metal complex being cleaved off before the labelled biological targeting moiety reaches the desired in vivo target site. The biological targeting moiety is therefore preferably covalently bound to the metal complexes of the present invention via linkages which are not readily metabolised (as are eg. ester linkages).

Preferred radiometal complexes of the present invention are symmetrical, ie. the two —$CR^2_2R^2_2NHCR^1_2C(=N—OH)R^1$ substituents on the —$CY(R^3)$— moiety are chosen to be the same. This has the advantage that, the radiometal complex does not contain a chiral centre, since such centres may generate diastereomeric radiometal complexes and possibly require the purification of particular isomers. It is also preferred that the radiometal complex of the chelator conjugate is electrically neutral.

It is believed that the $^{99m}Tc$ complexes of the chelators of the present invention are

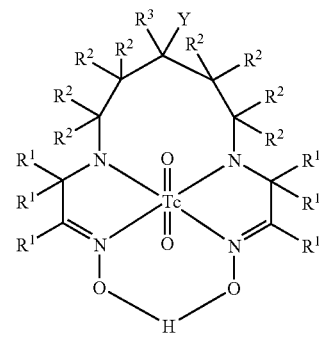

neutral, Tc(V) dioxo complexes as shown above.

In the $^{99m}Tc$-diaminedioxime complexes of the present invention, $R^3$ is preferably H. It is also preferred that at least one $R^2$ group is H, more preferably all the $R^2$ groups are H. Each $R^1$ is preferably $C_{1-3}$ alkyl, $C_{2-4}$ alkoxyalkyl, $C_{1-3}$ hydroxyalkyl, or $C_{1-3}$ fluoroalkyl, and is most preferably $C_{1-3}$ alkyl or $C_{1-3}$ fluoroalkyl. It is most especially preferred that all the $R^1$ groups are $CH_3$. Preferred Y groups for the $^{99m}Tc$ complex are as described above for the chelator conjugate.

Preferred radiometal complexes of the present invention wherein 2 or more R groups which, together with the atoms to which they are attached, form a carbocyclic, heterocyclic, saturated or unsaturated ring, comprise such rings having 3- to 6-members, especially 5- or 6-members. Most preferred such rings are saturated carbocyclic rings. Preferred carbocyclic rings are those in which 2 $R^1$ groups attached to either the same or adjacent carbon atoms are combined to form 3- to 6-membered, especially 5- or 6-membered saturated rings.

The radiometal complexes of the present invention may be prepared by reacting a solution of the radiometal in the appropriate oxidation state with the chelate conjugate at the appropriate pH. The solution may preferably contain a ligand which complexes weakly to the metal (such as gluconate or citrate) i.e. the radiometal complex is prepared by ligand exchange or transchelation. Such conditions are useful to suppress undesirable side reactions such as hydrolysis of the metal ion. When the radiometal ion is $^{99m}$Tc, the usual starting material is sodium pertechnetate from a $^{99}$Mo generator. Technetium is present in $^{99m}$Tc-pertechnetate in the Tc(VII) oxidation state, which is relatively unreactive. The preparation of technetium complexes of lower oxidation state Tc(I) to Tc(V) therefore usually requires the addition of a suitable pharmaceutically acceptable reducing agent such as sodium dithionite, sodium bisulphite, ascorbic acid, formamidine sulphinic acid, stannous ion, Fe(II) or Cu(I), to facilitate complexation. The pharmaceutically acceptable reducing agent is preferably a stannous salt, most preferably stannous chloride, stannous fluoride or stannous tartrate.

In a third aspect, the present invention provides radiopharmaceuticals which comprise the above radiometal complexes of the chelator conjugates in a sterile form suitable for human administration. Such radiopharmaceuticals are suitably supplied in either a container which is provided with a seal which is suitable for single or multiple puncturing with a hypodermic needle (e.g. a crimped-on septum seal closure) whilst maintaining sterile integrity. Such containers may contain single or multiple patient doses. Preferred multiple dose containers comprise a single bulk vial (e.g. of 10 to 30 cm$^3$ volume) which contains multiple patient doses, whereby single patient doses can thus be withdrawn into clinical grade syringes at various time intervals during the viable lifetime of the preparation to suit the clinical situation. Pre-filled syringes are designed to contain a single human dose, and are therefore preferably a disposable or other syringe suitable for clinical use. The pre-filled syringe may optionally be provided with a syringe shield to protect the operator from radioactive dose. Suitable such radiopharmaceutical syringe shields are known in the art and preferably comprise either lead or tungsten.

A $^{99m}$Tc radioactivity content suitable for a diagnostic imaging radiopharmaceutical is in the range 180 to 1500 MBq, depending on the site to be imaged in vivo, the uptake and the target to background ratio. For heart imaging with a $^{99m}$Tc radiopharmaceutical, ca. 1110 MBq (30 mCi) may be used for a stress study, and ca. 350 MBq (10 mCi) for a rest study.

In a fourth aspect, the present invention provides non-radioactive kits for the preparation of the $^{99m}$Tc radiopharmaceutical composition. Such kits are designed to give sterile radiopharmaceutical products suitable for human administration, e.g. via direct injection into the bloodstream. For $^{99m}$Tc, the kit is preferably lyophilised and is designed to be reconstituted with sterile $^{99m}$Tc-pertechnetate (TcO$_4^-$) from a $^{99m}$Tc radioisotope generator to give a solution suitable for human administration without further manipulation. Suitable kits comprise a container (eg. a septum-sealed vial) containing the chelator conjugate of Formula II in either free base or acid salt form, together with a pharmaceutically acceptable reducing agent such as sodium dithionite, sodium bisulphite, ascorbic acid, formamidine sulphinic acid, stannous ion, Fe(II) or Cu(I). The pharmaceutically acceptable reducing agent is preferably a stannous salt such as stannous chloride or stannous tartrate. Alternatively, the kit may optionally contain a metal complex which, upon addition of the radiometal, undergoes transmetallation (i.e. metal exchange) giving the desired product.

The non-radioactive kits may optionally further comprise additional components such as a transchelator, radioprotectant, antimicrobial preservative, pH-adjusting agent or filler. The "transchelator" is a compound which reacts rapidly to form a weak complex with technetium, then is displaced by the diaminedioxime. This minimises the risk of formation of reduced hydrolysed technetium (RHT) due to rapid reduction of pertechnetate competing with technetium complexation. Suitable such transchelators are salts of a weak organic acid, ie. an organic acid having a pKa in the range 3 to 7, with a biocompatible cation. Suitable such weak organic acids are acetic acid, citric acid, tartaric acid, gluconic acid, glucoheptonic acid, benzoic acid, phenols or phosphonic acids. Hence, suitable salts are acetates, citrates, tartrates, gluconates, glucoheptonates, benzoates, phenolates or phosphonates. Preferred such salts are tartrates, gluconates, glucoheptonates, benzoates, or phosphonates, most preferably phosphonates, most especially diphosphonates. A preferred such transchelator is a salt of MDP, ie. methylenediphosphonic acid, with a biocompatible cation.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (ie. 4-aminobenzoic acid), gentisic acid (ie. 2,5-dihydroxybenzoic acid) and salts thereof with a biocompatible cation as described above.

By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the radiopharmaceutical composition post-reconstitution, ie. in the radioactive diagnostic product itself. The antimicrobial preservative may, however, also optionally be used to inhibit the growth of potentially harmful micro-organisms in one or more components of the non-radioactive kit of the present invention prior to reconstitution. Suitable antimicrobial preservative(s) include: the parabens, ie. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the reconstituted kit is within acceptable limits (approximately pH 4.0 to 10.5) for human or mammalian administration. Suitable such pH-adjusting agents include pharmaceutically acceptable buffers, such as tricine, phosphate or TRIS [ie. tris(hydroxymethyl)aminomethane], and pharmaceutically acceptable bases such as sodium carbonate, sodium bicarbonate or mixtures thereof. When the conjugate of Formula II is employed in acid salt form, the pH adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars such as sucrose, maltose or trehalose.

In a fifth aspect the present invention provides bifunctional diaminedioxime chelators of Formula III useful to prepare chelator-biological targeting moiety conjugates:

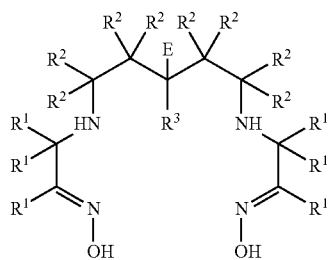

Formula III where:
each $R^1$, $R^2$ and $R^3$ is independently an R group;
E is -(A)$_n$-J
  where: J is a functional group suitable for conjugation to Z;
    -(A)$_n$- is a linker group where each A is independently —CR$_2$—, —CR=CR—, —C≡C—, —NRCO—, —CONR—, —SO$_2$NR—, —NRSO$_2$—, —CR$_2$OCR$_2$—, —CR$_2$SCR$_2$—, —CR$_2$NRCR$_2$—, a C$_{4-8}$ cycloheteroalkylene group, a C$_{4-8}$ cycloalkylene group, a C$_{5-12}$ arylene group, a C$_{3-12}$ heteroarylene group or a polyalkyleneglycol, polylactic acid or polyglycolic acid moiety;
    n is an integer of value 0 to 10;
each R group is independently H or C$_{1-10}$ alkyl, C$_{3-10}$ alkylaryl, C$_{2-10}$ alkoxyalkyl, C$_{1-10}$ hydroxyalkyl, C$_{1-10}$ fluoroalkyl, or 2 or more R groups, together with the atoms to which they are attached form a carbocyclic, heterocyclic, saturated or unsaturated ring.

By the term "functional group suitable for conjugation" is meant a functional group which will react with a corresponding functional group of Z (typically an amine, carboxyl or thiol group) to chemically link the diaminedioxime chelator to Z. Preferred such functional groups suitable for conjugation are: —NR$^5$R$^6$, —CO$_2$M, —NCS, —NCO, —SM$^1$, —OM$^1$, maleimide or acrylamide, where $R^5$ and $R^6$ are independently an R group or $P^G$; M is H, a cation, $P^G$ or an active ester; $M^1$ is H or $P^G$; and $P^G$ is a protecting group. The cation is suitably a positively-charged counterion, such as a metal ion, ammonium (NH$_4^+$) or quaternary ammonium or phosphonium ion. Preferably, the cation is a biocompatible cation. The terms 'biocompatible cation', 'active ester' and 'protecting group' are as defined above. When the functional group is —NR$^5$R$^6$, at least one and preferably both of $R^5$ and $R^6$ are H.

In the bifunctional chelators of Formula III of the present invention, $R^3$ is preferably H. It is also preferred that at least one $R^2$ group is H, more preferably all the $R^2$ groups are H. Each $R^1$ is preferably C$_{1-3}$ alkyl, C$_{2-4}$ alkoxyalkyl, C$_{1-3}$ hydroxyalkyl, or C$_{1-3}$ fluoroalkyl, and is most preferably C$_{1-3}$ alkyl or C$_{1-3}$ fluoroalkyl. It is most especially preferred that all the $R^1$ groups are CH$_3$.

Preferred bifunctional chelators wherein 2 or more R groups which, together with the atoms to which they are attached, form a carbocyclic, heterocyclic, saturated or unsaturated ring, comprise such rings having 3- to 6-members, especially 5- or 6-members. Most preferred such rings are saturated carbocyclic rings. Preferred carbocyclic rings are those in which 2 $R^1$ groups attached to either the same or adjacent carbon atoms are combined to form 3- to 6-membered, especially 5- or 6-membered saturated rings.

The chelator conjugates of Formula III may optionally be used in acid salt form, ie. where one or more amines of either the diaminedioxime donor set or the Y group are protonated with a biocompatible acid. Such salts may be obtained directly, eg. by HPLC purification employing such acids in the mobile phase (eg. acetic or trifluoroacetic acid), or by addition of the biocompatible acid to a solution of the chelator conjugate. The salt form may be useful to aid purification (eg. via precipitation or recrystallisation), or may facilitate dissolution in aqueous media (after which the pH can be readily adjusted if necessary).

Preferred linker groups -(A)$_n$ of the bifunctional chelator have a backbone chain of linked atoms which make up the -(A)$_n$ moiety contain 2 to 10 atoms, most preferably 2 to 5 atoms, with 2 or 3 atoms being especially preferred. A minimum linker group backbone chain of 2 atoms confers the advantage that, after conjugation, the chelator is well-separated from the biological targeting moiety so that any interaction is minimised. A further advantage is that the potential chelate ring size of the X and Z groups is so large (at least 8 for a 2 atom backbone chain) that these groups are unlikely to compete effectively with the coordination of the chelator to a radiometal.

Non-peptide linker groups such as alkylene groups or arylene groups have the advantage that there are no significant hydrogen bonding interactions with the conjugated biological targeting moiety so that the linker does not wrap round onto the biological targeting moiety. Preferred alkylene spacer groups are —(CH$_2$)$_n$— where n is 2 to 5. Preferred arylene spacers are of formula:

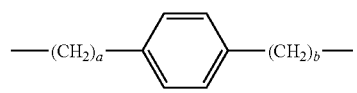

where: a and b are independently 0, 1 or 2.

A preferred E group is thus —CH$_2$CH$_2$-J, most preferably —CH$_2$CH$_2$—NHR$^5$ or —CH$_2$CH$_2$—CO$_2$H or active esters thereof, with E=—CH$_2$CH$_2$—NH$_2$ being especially preferred. The acid can also be converted to a mixed anhydride eg. by reacting with isobutylchloroformate and base. The mixed anhydride also reacts with nucleophiles such as amines. The grouping E=—CH$_2$CH$_2$—NH$_2$ has the additional advantage that it stems from the intermediate R$^3$C(CH$_2$CH$_2$NH$_2$)$_3$, preferably the intermediate HC(CH$_2$CH$_2$NH$_2$)$_3$, which being symmetrical is much easier to synthesise, since triamines having different chain lengths would require the use of synthetic strategies to chemically distinguish the various amines (eg. via protecting groups).

Preferred bifunctional diaminedioxime chelators of Formula III of the present invention are symmetrical, ie. the two —C(R$^2$)$_2$(R$^2$)$_2$NHCR$^1$$_2$C(=N—OH)R$^1$ substituents on the —CY(R$^3$)— moiety are chosen to be the same. This has the advantage that, the chelator does not contain a chiral centre, since such centres may generate diastereomeric radiometal complexes and possibly require the purification of particular isomers. An especially preferred bifunctional diaminedioxime chelator has the formula:

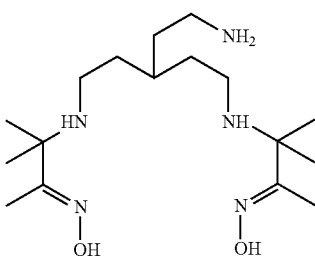 [SMILES: C/C(=N\O)C(C)(C)NCCC(CCN)CCNC(C)(C)/C(C)=N/O]

Acid salts of this compound are also within the scope of the present invention.

The bifunctional diaminedioxime chelators of the present invention may suitably be prepared by alkylation of a compound of Formula IV:

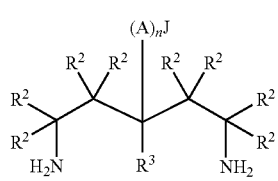

Formula IV where A, J, $R^2$, $R^3$ and n are as defined for Formula III above, with either:

(i) the appropriate chloronitroso derivative Cl—$C(R^1)_2$—CH(NO)$R^1$;

(ii) an alpha-chloro oxime of formula Cl—$C(R^1)_2$—C(=NOH)$R^1$;

(iii) an alpha-bromoketone of formula Br—$C(R^1)_2$—C(=O)$R^1$ followed by conversion of the diaminediketone product to the diaminedioxime with hydroxylamine.

Route (i) is described by S. Jurisson et al [Inorg. Chem., 26, 3576-82 (1987]. Chloronitroso compounds can be obtained by treatment of the appropriate alkene with nitrosyl chloride (NOCl) as is described in Example 3. Further synthetic details of chloronitroso compounds are given by: Ramalingam, K. et al Synth. Commun. (1995) 25(5) 743-52; Glaser et al J. Org. Chem. (1996), 61(3), 1047-48; Clapp, Leallyn B.; et al J. Org. Chem. (1971), 36(8) 1169-70; Saito, Giulichi et al Shizen Kagaku (1995), 47, 41-9 and Schulz, Manfred Z. Chem (1981), 21(11), 404-5. Route (iii) is described in broad terms by Nowotnik et al [Tetrahedron, 50(29), p. 8617-8632 (1994)]. Alpha-chloro-oximes can be obtained by oximation of the corresponding alpha-chloro-ketone or aldehyde, which are commercially available. Alpha-bromoketones are commercially available.

When J is —$NH_2$, the triamine of Formula IV may optionally first be mono-protected such that the J group primary amine is protected. The diaminedioxime is then prepared according to routes (i), (ii) or (iii) above, then the protecting group is removed. Suitable protecting groups are known in the art, and include BOC (ie. tert-butoxycarbonyl) or Fmoc as described above.

Compounds of Formula IV are suitably prepared from $HC(CH_2CH_2OAc)_3$ by hydrolysing one or more of the acetate esters to a primary alcohol(s) and converting to a leaving group such as a methanesulphonate ester with methanesulphonyl chloride and pyridine. This leaving group may then be displaced with a suitable nucleophile that may be converted to the desired functionality. To generate a carboxylic acid (ie. J=—$CO_2H$) a cyanide anion would be used. Acid hydrolysis of the cyanide would generate the desired carboxylic acid. To generate an amine, an azide nucleophile would be used to generate an alkyl azide. Hydrogenation of the alkyl azide would produce an amine. To generate a thiol (ie. J=—SH), displacement of the leaving group with thioacetic acid anion would give a thioacetate which on acid hydrolysis would produce the thiol.

In a further aspect the present invention provides a compound of Formula V:

$$HC(CH_2CH_2NR^7R^8)_3, \qquad \text{Formula V}$$

where $R^7$ and $R^8$ are independently H or $P^G$, or $R^7$ and $R^8$ together form $P^G$; or a salt thereof.

$P^G$ is a protecting group as defined above. The compounds of Formula V are useful precursors to a range of bifunctional chelators of the present invention. A preferred compound of Formula V is $HC(CH_2CH_2NH_2)_2(CH_2CH_2NR^7R^8)$, ie. a mono-protected triamine as described above. Most preferably, all the $R^7$ and $R^8$ groups are H, ie. the compound $HC(CH_2CH_2NH_2)_3$, or an acid salt thereof, is a preferred compound of the present invention.

FIG. 1 shows the chemical structures of Compounds 1 to 6.
FIG. 2 shows the chemical structure of Compound 5 in full.
FIG. 3 shows the reaction scheme for the azide synthesis of 1,1,1-tris(2-aminoethyl)amine of Example 1.
FIG. 4 shows the reaction scheme for the alternative synthesis of 1,1,1-tris(2-aminoethyl)amine of Example 2.

The invention is illustrated by the non-limiting Examples detailed below. Example 1 describes the synthesis of the novel compound 1,1,1-tris(2-aminoethyl)methane. Example 2 provides an alternative synthesis of 1,1,1-tris(2-aminoethyl)methane which avoids the use of potentially hazardous azide intermediates. Example 3 describes the synthesis of various chloronitrosoalkane precursors. Example 4 describes the synthesis of a preferred amine-substituted bifunctional diaminedioxime of the present invention (Compound 1). Example 5 describes the synthesis of a benzamide conjugate (Compound 2) of Compound 1. Example 6 shows how a spacer group can be introduced which effectively converts the terminal amine function of the bifunctional chelator to a terminal carboxyl function. Example 7 describes the solid phase synthesis of a thrombus-targeting peptide. Example 8 provides a synthesis of Compound 5, ie. a conjugate of Compound 1 with a targeting peptide. Example 9 describes the synthesis of Compounds 7 and 8, which are diaminedioxime analogues incorporating ring structures.

Example 10 compares the $^{99m}$Tc-radiolabelling of Compound 2 with that of the aza analogue prior art chelator (Compound 3), and shows that the chelators of the present invention give much more efficient and rapid labelling under milder conditions, ie. room temperature and at less alkaline pH. Thus, the prior art chelator requires pH 10 and a time of at least 120 min at room temperature to give RCP's of over 80%, whereas Compound 3 labels at over 95% RCP within 15 minutes. Example 11 shows that Compound 5 labels with $^{99m}$Tc to give a high radiochemical purity preparation. Example 12 shows that $^{99m}$Tc-labelled Compound 5 shows comparable blood clot uptake in vitro to the prior art compound $^{99m}$Tc-Compound 6, and that hence the biological targeting properties of the peptide are retained when conjugated to the diaminedioxime chelators of the present invention. Example 13 shows the $^{99m}$Tc radiolabelling under mild conditions of Compound 9, which is a conjugate of Compound 1 with a cyclic peptide having relatively sensitive disulphide bonds.

Example 1

Synthesis of 1,1,1-tris(2-aminoethyl)methane

Step 1(a): 3(methoxycarbonylmethylene)glutaric acid dimethylester

Carbomethoxymethylenetriphenylphosphorane (167 g, 0.5 mol) in toluene (600 ml) was treated with dimethyl 3-oxoglutarate (87 g, 0.5 mol) and the reaction heated to 100° C. on an oil bath at 120° C. under an atmosphere of nitrogen for 36 h. The reaction was then concentrated in vacuo and the oily residue triturated with 40/60 petrol ether/diethylether 1:1, 600 ml. Triphenylphosphine oxide precipitated out and the supernatant liquid was decanted/filtered off. The residue on evaporation in vacuo was Kugelrohr distilled under high vacuum Bpt (oven temperature 180-200° C. at 0.2 torr) to give 3-(methoxycarbonylmethylene)glutaric acid dimethylester (89.08 g, 53%).

NMR $^1$H(CDCl$_3$): δ 3.31 (2H, s, CH$_2$), 3.7 (9H, s, 3×OCH$_3$), 3.87 (2H, s, CH$_2$), 5.79 (1H, s, =CH), ppm.

NMR $^{13}$C(CDCl$_3$), δ 36.56, CH$_3$, 48.7, 2×CH$_3$, 52.09 and 52.5 (2×CH$_2$); 122.3 and 146.16 C=CH; 165.9, 170.0 and 170.5 3×COO ppm.

Step 1(b): Hydrogenation of 3-(methoxycarbonylmethylene)glutaric acid dimethylester 3-(methoxycarbonylmethylene)glutaric acid dimethylester (89 g, 267 mmol) in methanol (200 ml) was shaken with (10% palladium on charcoal: 50% water) (9 g) under an atmosphere of hydrogen gas (3.5 bar) for (30 h). The solution was filtered through kieselguhr and concentrated in vacuo to give 3-(methoxycarbonylmethyl)glutaric acid dimethylester as an oil, yield (84.9 g, 94%).

NMR $^1$H(CDCl$_3$), δ 2.48 (6H, d, J=8 Hz, 3×CH$_2$), 2.78 (1H, hextet, J=8 Hz CH) 3.7 (9H, s, 3×CH$_3$).

NMR $^{13}$C(CDCl$_3$), δ 28.6, CH; 37.50, 3×CH$_3$; 51.6, 3×CH$_2$; 172.28, 3×COO.

Step 1(c): Reduction and esterification of trimethyl ester to the triacetate Under an atmosphere of nitrogen in a 3 necked 2 L round bottomed flask lithium aluminium hydride (20 g, 588 mmol) in tetrahydrofuran (400 ml) was treated cautiously with tris(methyloxycarbonylmethyl)methane (40 g, 212 mmol) in tetrahydrofuran (200 ml) over 1 h. A strongly exothermic reaction occurred, causing the solvent to reflux strongly. The reaction was heated on an oil bath at 90° C. at reflux for 3 days. The reaction was quenched by the cautious dropwise addition of acetic acid (100 ml) until the evolution of hydrogen ceased. The stirred reaction mixture was cautiously treated with acetic anhydride solution (500 ml) at such a rate as to cause gentle reflux. The flask was equipped for distillation and stirred and then heating at 90° C. (oil bath temperature) to distil out the tetrahydrofuran. A further portion of acetic anhydride (300 ml) was added, the reaction returned to reflux configuration and stirred and heated in an oil bath at 140° C. for 5 h. The reaction was allowed to cool and filtered. The aluminium oxide precipitate was washed with ethyl acetate and the combined filtrates concentrated on a rotary evaporator at a water bath temperature of 50° C. in vacuo (5 mmHg) to afford an oil. The oil was taken up in ethyl acetate (500 ml) and washed with saturated aqueous potassium carbonate solution. The ethyl acetate solution was separated, dried over sodium sulphate, and concentrated in vacuo to afford an oil. The oil was Kugelrohr distilled in high vacuum to give tris(2-acetoxyethyl)methane (45.3 g, 95.9%) as an oil. Bp. 220° C. at 0.1 mmHg.

NMR $^1$H(CDCl$_3$), δ 1.66 (7H, m, 3×CH$_2$, CH), 2.08 (1H, s, 3×CH$_3$); 4.1 (6H, t, 3×CH$_2$O).

NMR $^{13}$C(CDCl$_3$), δ 20.9, CH$_3$; 29.34, CH; 32.17, CH$_2$; 62.15, CH$_2$O; 171, CO.

Step 1(d): Removal of Acetate groups from the triacetate

Tris(2-acetoxyethyl)methane (45.3 g, 165 mM) in methanol (200 ml) and 880 ammonia (100 ml) was heated on an oil bath at 80° C. for 2 days. The reaction was treated with a further portion of 880 ammonia (50 ml) and heated at 80° C. in an oil bath for 24 h. A further portion of 880 ammonia (50 ml) was added and the reaction heated at 80° C. for 24 h. The reaction was then concentrated in vacuo to remove all solvents to give an oil. This was taken up into 880 ammonia (150 ml) and heated at 80° C. for 24 h. The reaction was then concentrated in vacuo to remove all solvents to give an oil. Kugelrohr distillation gave acetamide bp 170-180 0.2 mm. The bulbs containing the acetamide were washed clean and the distillation continued. Tris(2-hydroxyethyl)methane (22.53 g, 92%) distilled at bp 220° C. 0.2 mm.

NMR $^1$H(CDCl$_3$), δ 1.45 (6H, q, 3×CH$_2$), 2.2 (1H, quintet, CH); 3.7 (6H, t 3×CH$_2$OH); 5.5 (3H, brs, 3×OH).

NMR $^{13}$C(CDCl$_3$), δ 22.13, CH; 33.95, 3×CH$_2$; 57.8, 3×CH$_2$OH.

Step 1(e): Conversion of the triol to the tris(methanesulphonate)

To an stirred ice-cooled solution of tris(2-hydroxyethyl)methane (10 g, 0.0676 mol) in dichloromethane (50 ml) was slowly dripped a solution of methanesulphonyl chloride (40 g, 0.349 mol) in dichloromethane (50 ml) under nitrogen at such a rate that the temperature did not rise above 15° C. Pyridine (21.4 g, 0.27 mol, 4 eq) dissolved in dichloromethane (50 ml) was then added drop-wise at such a rate that the temperature did not rise above 15° C., exothermic reaction. The reaction was left to stir at room temperature for 24 h and then treated with 5N hydrochloric acid solution (80 ml) and the layers separated. The aqueous layer was extracted with further dichloromethane (50 ml) and the organic extracts combined, dried over sodium sulphate, filtered and concentrated in vacuo to give tris[2-(methylsulphonyloxy)ethyl]methane contaminated with excess methanesulphonyl chloride. The theoretical yield was 25.8 g.

NMR $^1$H(CDCl$_3$), δ 4.3 (6H, t, 2×CH$_2$), 3.0 (9H, s, 3×CH$_3$), 2 (1H, hextet, CH), 1.85 (6H, q, 3×CH$_2$).

Step 1(f): Preparation of 1,1,1-tris(2-azidoethyl)methane

A stirred solution of tris[2-(methylsulphonyloxy)ethyl]methane [from Step 1(e), contaminated with excess methylsulphonyl chloride] (25.8 g, 67 mmol, theoretical) in dry DMF (250 ml) under nitrogen was treated with sodium azide (30.7 g, 0.47 mol) portion-wise over 15 minutes. An exotherm was observed and the reaction was cooled on an ice bath. After 30 minutes, the reaction mixture was heated on an oil bath at 50° C. for 24 h. The reaction became brown in colour. The reaction was allowed to cool, treated with dilute potassium carbonate solution (200 ml) and extracted three times with 40/60 petrol ether/diethylether 10:1 (3×150 ml). The organic extracts were washed with water (2×150 ml), dried over sodium sulphate and filtered. Ethanol (200 ml) was added to the petrol/ether solution to keep the triazide in solution and the volume reduced in vacuo to no less than 200 ml. Ethanol (200 ml) was added and reconcentrated in vacuo to remove the last traces of petrol leaving no less than 200 ml of ethanolic solution. The ethanol solution of triazide was used directly in Step 1(g).
CARE: DO NOT REMOVE ALL THE SOLVENT AS THE AZIDE IS POTENTIALLY EXPLOSIVE AND SHOULD BE KEPT IN DILUTE SOLUTION AT ALL TIMES.

Less than 0.2 ml of the solution was evaporated in vacuum to remove the ethanol and an NMR run on this small sample:
NMR $^1$H(CDCl$_3$), δ 3.35 (6H, t, 3×CH$_2$), 1.8 (1H, septet, CH), 1.6 (6H, q, 3×CH$_2$).

Step 1(g): Preparation of 1,1,1-tris(2-aminoethyl)methane

Tris(2-azidoethyl)methane (15.06 g, 0.0676 mol), (assuming 100% yield from previous reaction) in ethanol (200 ml) was treated with 10% palladium on charcoal (2 g, 50% water) and hydrogenated for 12 h. The reaction vessel was evacuated every 2 hours to remove nitrogen evolved from the reaction and refilled with hydrogen. A sample was taken for NMR analysis to confirm complete conversion of the triazide to the triamine. Caution: unreduced azide could explode on distillation. The reaction was filtered through a celite pad to remove the catalyst and concentrated in vacuo to give tris(2-aminoethyl)methane as an oil. This was further purified by Kugelrohr distillation bp. 180-200° C. at 0.4 mm/Hg to give a colourless oil (8.1 g, 82.7% overall yield from the triol).
NMR $^1$H(CDCl$_3$), 2.72 (6H, t, 3×CH$_2$N), 1.41 (H, septet, CH), 1.39 (6H, q, 3×CH$_2$).
NMR $^{13}$C(CDCl$_3$), δ 39.8 (CH$_2$NH$_2$), 38.2 (CH$_2$), 31.0 (CH).

Example 2

Alternative Preparation of 1,1,1-tris(2-aminoethyl)methane

Step 2(a): Amidation of trimethylester with p-methoxy-benzylamine

Tris(methyloxycarbonylmethyl)methane [2 g, 8.4 mmol; prepared as in Step 1(b) above] was dissolved in p-methoxybenzylamine (25 g, 178.6 mmol). The apparatus was set up for distillation and heated to 120° C. for 24 hrs under nitrogen flow. The progress of the reaction was monitored by the amount of methanol collected. The reaction mixture was cooled to ambient temperature and 30 ml of ethyl acetate was added, then the precipitated triamide product stirred for 30 min. The triamide was isolated by filtration and the filter cake washed several times with sufficient amounts of ethyl acetate to remove excess p-methoxy-benzylamine. After drying 4.6 g, 100%, of a white powder was obtained. The highly insoluble product was used directly in the next step without further purification or characterization.

Step 2(b): Preparation of 1,1,1-tris[2-(p-methoxybenzylamino)ethyl]methane

To a 1000 ml 3-necked round bottomed flask cooled in a ice-water bath the triamide from step 2(a) (10 g, 17.89 mmol) is carefully added to 250 ml of 1M borane solution (3.5 g, 244.3 mmol) borane. After complete addition the ice-water bath is removed and the reaction mixture slowly heated to 60° C. The reaction mixture is stirred at 60° C. for 20 hrs. A sample of the reaction mixture (1 ml) was withdrawn, and mixed with 0.5 ml 5N HCl and left standing for 30 min. To the sample 0.5 ml of 50 NaOH was added, followed by 2 ml of water and the solution was stirred until all of the white precipitate dissolved. The solution was extracted with ether (5 ml) and evaporated. The residue was dissolved in acetonitrile at a concentration of 1 mg/ml and analysed by MS. If mono- and diamide (M+H/z=520 and 534) are seen in the MS spectrum, the reaction is not complete. To complete the reaction, a further 100 ml of 1M borane THF solution is added and the reaction mixture stirred for 6 more hrs at 60° C. and a new sample withdrawn following the previous sampling procedure. Further addition of the 1M borane in THF solution is continued as necessary until there is complete conversion to the triamine.

The reaction mixture is cooled to ambient temperature and 5N HCl is slowly added, [CARE: vigorous foam formation occurs!]. HCl is added until no more gas evolution is observed. The mixture is stirred for 30 min and then evaporated. The cake is suspended in aqueous NaOH solution (20-40%; 1:2 w/v) and stirred for 30 minutes. The mixture is then diluted with water (3 volumes). The mixture was then extracted with diethylether (2×150 ml) [CARE: do not use halogenated solvents]. The combined organic phases were then washed with water (1×200 ml), brine (150 ml) and dried over magnesium sulphate. Yield after evaporation: 7.6 g, 84% as oil.
NMR $^1$H(CDCl$_3$), δ: 1.45, (6H, m, 3×CH$_2$; 1.54, (1H, septet, CH); 2.60 (6H, t, 3×CH$_2$N); 3.68 (6H, s, ArCH$_2$); 3.78 (9H, s, 3×CH$_3$O); 6.94 (6H, d, 6×Ar); 7.20 (6H, d, 6×Ar).
NMR $^{13}$C(CDCl$_3$), δ: 32.17, CH; 34.44, CH$_2$; 47.00, CH$_2$; 53.56, ArCH$_2$; 55.25, CH$_3$O; 113.78, Ar; 129.29, Ar; 132.61; Ar; 158.60, Ar;

Step 2(c): Preparation of 1,1,1-tris(2-aminoethyl)methane 1,1,1-tris[2-(β-methoxybenzylamino)ethyl]methane (20.0 gram, 0.036 mol) was dissolved in methanol (100 ml) and Pd(OH)$_2$ (5.0 gram) was added. The mixture was hydrogenated (3 bar, 100° C., in an autoclave) and stirred for 5 hours. Pd(OH)$_2$ was added in two more portions (2×5 gram) after 10 and 15 hours respectively.

The reaction mixture was filtered and the filtrate was washed with methanol. The combined organic phase was evaporated and the residue was distilled under vacuum (1×10$^{-2}$, 110° C.) to give 2.60 gram (50%) of 1,1,1-tris(2-aminoethyl)methane identical with the previously described Example 1.

Example 3

Preparation of 3-chloro-3-methyl-2-nitrosobutane

A mixture of 2-methylbut-2-ene (147 ml, 1.4 mol) and isoamyl nitrite (156 ml, 1.16 mol) was cooled to −30° C. in a bath of cardice and methanol and vigorously stirred with an overhead air stirrer and treated dropwise with concentrated hydrochloric acid (140 ml, 1.68 mol) at such a rate that the temperature was maintained below −20° C. This requires about 1 h as there is a significant exotherm and care must be taken to prevent overheating. Ethanol (100 ml) was added to reduce the viscosity of the slurry that had formed at the end of the addition and the reaction stirred at −20 to −10° C. for a further 2 h to complete the reaction. The precipitate was collected by filtration under vacuum and washed with 4×30 ml of cold (−20° C.) ethanol and 100 ml of ice cold water, and dried in vacuo to give 3-chloro-3-methyl-2-nitrosobutane as a white solid. The ethanol filtrate and washings were combined and diluted with water (200 ml) and cooled and allowed to stand for 1 h at −10° C. when a further crop of 3-chloro-3-methyl-2-nitrosobutane crystallised out. The precipitate was collected by filtration and washed with the minimum of water and dried in vacuo to give a total yield of 3-chloro-3-methyl-2-nitrosobutane (115 g 0.85 mol, 73%)>98% pure by NMR.

NMR $^1$H(CDCl$_3$), As a mixture of isomers (isomer1, 90%) 1.5 d, (2H, CH$_3$), 1.65 d, (4H, 2×CH$_3$), 5.85, q, and 5.95, q, together 1H. (isomer2, 10%), 1.76 s, (6H, 2×CH$_3$), 2.07 (3H, CH$_3$).

1-Chloro-1-(1-nitrosoethyl)cyclopentane was prepared in an analogous manner from ethylidenecyclopentane (yield 55%) [J. Org. Chem., 36(8) p. 1169-70].

1-Chloro-1-(1-nitrosoethyl)cyclohexane was prepared in an analogous manner from ethylidenecyclohexane (yield 63%) [J. Org. Chem., 36(8) p. 1169-70].

$\delta_H$ (CDCl$_3$; 270 MHz), 1.52 (3H, d J$_{HH}$ 7 Hz, CH$_3$), 1.48-2.20 (10H, m, CH$_2$×5), 5.96 (1H, q, J$_{HH}$ 7 Hz, CH).

1-Chloro-1-methyl-2-nitroso-cyclohexane was prepared in an analogous manner from 1-methyl-1-cyclohexene (yield 57%) [Ind J. Chem Sect B (1978) 16B(10) 917-20, Z. Chem. (1981), 21(11) 404-5, J. Pract. Chem. (1978) 320(3) 433-51].

$\delta_H$ (CDCl$_3$; 270 MHz), 1.41-2.28 (11H, m, CH$_3$, CH$_2$×4), 5.72-5.79 (1H, m, CH).

Example 4

Synthesis of bis[N-(1,1-dimethyl-2-N-hydroxyimine propyl)-2-aminoethyl]-(2-aminoethyl)methane (Compound 1)

To a solution of tris(2-aminoethyl)methane (4.047 g, 27.9 mmol) in dry ethanol (30 ml) was added potassium carbonate anhydrous (7.7 g, 55.8 mmol, 2 eq) at room temperature with vigorous stirring under a nitrogen atmosphere. A solution of 3-chloro-3-methyl-2-nitrosobutane (7.56 g, 55.8 mol, 2 eq) was dissolved in dry ethanol (100 ml) and 75 ml of this solution was dripped slowly into the reaction mixture. The reaction was followed by TLC on silica [plates run in dichloromethane, methanol, concentrated (0.88 sg) ammonia; 100/30/5 and the TLC plate developed by spraying with ninhydrin and heating]. The mono-, di- and tri-alkylated products were seen with RF's increasing in that order. Analytical HPLC was run using RPR reverse phase column in a gradient of 7.5-75% acetonitrile in 3% aqueous ammonia. The reaction was concentrated in vacuo to remove the ethanol and resuspended in water (10 ml). The aqueous slurry was extracted with ether (100 ml) to remove some of the trialkylated compound and lipophilic impurities leaving the mono and desired dialkylated product in the water layer. The aqueous solution was buffered with ammonium acetate (2 eq, 4.3 g, 55.8 mmol) to ensure good chromatography. The aqueous solution was stored at 4° C. overnight before purifying by automated preparative HPLC.

Yield (2.2 g, 6.4 mmol, 23%).

Mass spec; Positive ion 10 V cone voltage. Found: 344; calculated M+H=344.

NMR $^1$H(CDCl$_3$), δ 1.24 (6H, s, 2×CH$_3$), 1.3 (6H, s, 2×CH$_3$), 1.25-1.75 (7H, m, 3×CH$_2$, CH), (3H, s, 2×CH$_2$), 2.58 (4H, m, CH$_2$N), 2.88 (2H, t CH$_2$N$_2$), 5.0 (6H, S, NH$_2$, 2×NH, 2×OH).

NMR $^1$H((CD$_3$)$_2$SO) δ 1.14×CH; 1.29, 3×CH$_2$; 2.1 (4H, t, 2×CH$_2$);

NMR $^{13}$C((CD$_3$)$_2$SO), δ 9.0 (4×CH$_3$), 25.8 (2×CH$_3$), 31.0 2×CH$_2$, 34.6 CH$_2$, 56.8 2×CH$_2$N; 160.3; C=N.

HPLC conditions: flow rate 8 ml/min using a 25 mm PRP column
A=3% ammonia solution (sp.gr=0.88)/water.
B=Acetonitrile

| Time | % B |
|------|------|
| 0 | 7.5 |
| 15 | 75.0 |
| 20 | 75.0 |
| 22 | 7.5 |
| 30 | 7.5 |

Load 3 ml of aqueous solution per run, and collect in a time window of 12.5-13.5 min.

Example 5

The Preparation of Compound 2

The Benzamide Conjugate of Compound 1

Compound 1 (0.5 g, 1.45 mmol) in dry acetonitrile (50 ml) and triethylamine (150 mg, 1.45 mmol) under an atmosphere of nitrogen was cooled on an ice bath to 0° C. Benzoic anhydride (330 mg, 1.45 mmol) was added to the stirred reaction and allowed to warm to room temperature and left to stir overnight. The acetonitrile was removed in vacuo and the residue redissolved in (50 ml) dichloromethane, washed with aqueous potassium carbonate (2×50 ml), separated and dried over sodium sulphate. The aqueous potassium carbonate solution was extracted with dichloromethane (2×50 ml), dried over sodium sulphate, and the combined dichloromethane extracts concentrated in vacuo to a gum. Analytical HPLC indicated that the product was not as pure as required and the material was therefore purified by automated preparative HPLC, giving Compound 2. The product analysed as one spot on both TLC and analytical HPLC.

HPLC conditions: flow rate of 8 ml/min using a 150 mm×25 mm PRP column;
Sample loaded in 2 ml of 30% ethanol water per run.
A=3% ammonia solution (sp.gr=0.88)/water.
B=Acetonitrile

| Time | % B |
|------|------|
| 0 | 7.5 |
| 15 | 75.0 |
| 20 | 75.0 |
| 22 | 7.5 |
| 30 | 7.5 |

The required product eluted at 15.25-16.5 min. The product solution was evaporated in vacuo to give (304 mg, 0.68 mmol, 47%) of a colourless glassy foam m.p. 55° C.

NMR $^1$H(CDCl$_3$), 1.26 (12H, s, 4×CH$_3$), 1.43 (2H, m, CH$_2$), 1.57 (4H, m, CH$_2$), 1.75 (1H, m, CH), 1.823 (6H, s, 2×CH$_3$), 2.58, (4H, m, 2×CH$_2$N), 3.56 (2H, m, CH$_2$NHCO), 6.95 (1H, m, NHCO), 7.42 (3H, m, 3×ArH) 7.79 (2H, d, ArH).

NMR $^{13}$C(CDCl$_3$) 10.09, 25.7, 26.1, 28.5, 32.8, 33.3, 37.93, 75.57, 127.0, 128.4, 131.4, 158.98, 168.15.

M/S C$_{24}$H$_{41}$N$_5$O$_3$ M+H=448 Found 448

RF 0.8 in 100:30:5/CH$_2$Cl$_2$:MeOH: 880 Ammonia, visualised with ninhydrin.

Example 6

Synthesis of bis[(1,1-dimethyl-2-N-hydroxyimine propyl)2-aminoethyl]-(2-(Glutarylamide)ethyl)methane [Compound 4; the glutarylamide derivative of Compound 1]

Compound 1 (0.5 g, 1.45 mmol) in dry acetonitrile (50 ml) and triethylamine (150 mg, 1.45 mmol) under an atmosphere of nitrogen was cooled on an ice bath to 0° C. Glutaric anhydride (165 mg, 1.45 mmol) was added to the stirred reaction and allowed to warm to room temperature and left to stir overnight. The precipitate that formed overnight was collected by filtration and dried in vacuo to give an impure sample of the title compound (267 mg, 0.583 mmol, 40%). The filtrate was concentrated in vacuo to give a colourless glass which together with the precipitate that had been collected was redissolved in 5% 0.880 sg ammonia, water (50 ml) and purified by automated preparative HPLC.

HPLC conditions: flow rate 8 ml/min, using a 150 mm×25 mm PRP column
Sample loaded in 2 ml of solution per run.
A=3% ammonia solution (sp.gr=0.88)/water.
B=Acetonitrile

| Time | % B |
|------|-----|
| 0    | 7.5 |
| 15   | 75.0 |
| 20   | 75.0 |
| 22   | 7.5 |
| 31   | 7.5 |

The required product eluted at 15.25-16.5 min. The product solution was evaporated in vacuo to give (304 mg, 0.68 mmol, 47%) of a colourless glassy foam m.p. 54.8° C. The product analysed as one spot on both TLC and analytical HPLC.

NMR $^1$H(DMSO), 0.7 (12H, s, 4×CH$_3$), 0.85 (4H, m, 2×CH$_2$), 1.0 (1H, m, CH), 1.3 (6H, s, 2×CH$_3$), 1.3 (4H, m, 2×CH$_2$), 1.6 (2H, m, CH$_2$), 1.75 (6, m, 3×CH$_2$), 2.6 (2, m, 2×OH) 3.2 (2H, t, NH) 7.3 (1H, t, NH).

NMR $^{13}$C(CD$_3$SO) 8.97, 20.51, 20.91, 25.09, 25.60, 31.06, 33.41, 33.86, 56.89, 66.99, 160.07, 1712.34, 174.35, 174.56

M/S C$_{22}$H$_{43}$N$_5$O$_5$ M+H=457 Found 457.6

Example 7

Synthesis of the Protected Peptide Ac-NQEQVSP(3-I)YTLLKG

The protected peptide Ac-Asn(Trt)-Gln(Trt)-Glu(OtBu)-Gln(Trt)-Val-Ser(tBu)-Pro-Tyr(3I)-Thr(tBu)-Leu-Leu-Lys(Boc)-Gly-OH was assembled on a 2-chlorotrityl solid phase resin by anchoring Fmoc-Gly- to the resin, and then successive deprotections/coupling cycles with the appropriate protected amino acids and the coupling reagents DCCI and HOBt. The terminal asparagine is acetylated, cleaved from the resin using 0.5% TFA and the peptide was used without further purification.

Example 8

Synthesis of Compound 5—A Peptide Conjugate of Compound 1

The protected Ac-NQEQVSPY(3I)TLLKG peptide of Example 7 was cleaved from the solid phase resin, and then coupled with Compound 1 in solution using Benzotriazole-1-yl-oxytris-pyrrolidino-phosphonium hexafluorophosphate and 1-hydroxybenzotriazole as the coupling agents. Compound 5 was obtained by deprotection in reagent K (reagent K is 82.5% TFA, 5% phenol, 5% processed water, 5% thioanisole, 2.5% ethanedithiol). The crude peptide was first purified by RP-HPLC using TFA followed by a second purification and salt exchange with acetic acid, lyophilisation, filtration with a 0.22µ filter and a final lyophilisation to give Compound 5.

The prior art aza-diaminedioxime chelate conjugate (Compound 6—see FIG. 1) of the same peptide, ie. Ac-NQEQVSPY(3I)TLLKG was prepared in the same manner for comparison.

Example 9

Preparation of 1-(1-{3-(2-Aminoethyl)-5-[1-(1-hydroxyliminoethyl)cyclohexylamino]pentylamino}cyclohexyl)ethanone dioxime [Compound 7]

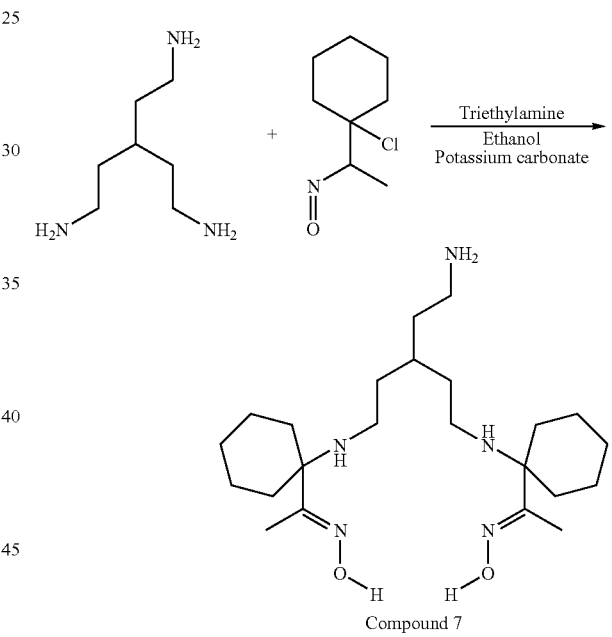

Compound 7

To a solution of 1,1,1-tris(2-aminoethyl)methane (0.96 g, 6.6 mmol) in dry ethanol (7.5 ml) was added potassium carbonate (anhydrous) (1.8 g, 13 mmol) and triethylamine (1.33 g, 13 mmol) at room temperature with vigorous stirring under a nitrogen atmosphere. A solution of 1-chloro-1-(1-nitrosoethyl)cyclohexane (2.3 g, 13 mmol) in dichloromethane (30 ml) was added dropwise over 1 h. The mixture was then left to stir at room temperature for 18 h. The solvent was then removed under reduced pressure. Water (30 ml) and ether (25 ml) were then added to the reaction residue. The aqueous phase and the organic phase were then separated.

HPLC:
ISOCRATIC: 90% B (MeOH) 10% (NH$_3$ 3%). Ether extract: HPLC showed two major bands-first band: dioxime, second band: trioxime. Dioxime: (0.55 g, 20%), FAB m/z 424 (M+H), HRMS: Found: 424.3642, calc'd: 424.3652 (C$_{23}$H$_{45}$N$_5$O$_2$).

NMR:

$\delta_H$(CDCl$_3$; 270 MHz), 1.34-1.72 (33H, m, CH, CH$_2$×13, CH$_3$×2), 2.18-2.33 (4H, m, NCH$_2$×2), 2.56-2.69 (2H, m, NCH$_2$).

The compound 1-(1-{3-(2-aminoethyl)-5-[1-(1-hydroxyiminoethyl)cyclohexylamino]pentylamino}cyclohexyl) ethanone dioxime [Compound 8] was prepared in an analogous manner:

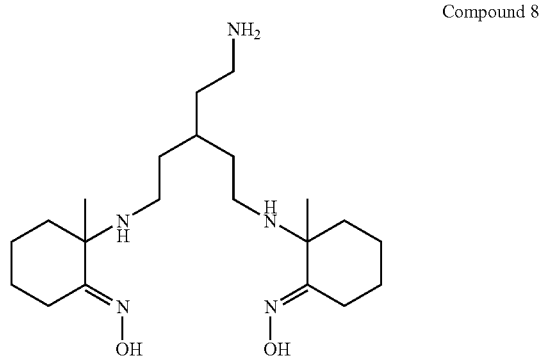 [SMILES: CC1(NCCC(CCN)CCNC2(C)CCCC/C2=N\O)CCCC/C1=N\O]

Compound 8

FAB m/z 396 (M+H), HRMS: Found: 396.3322, calc'd: 396.3339; (C$_{21}$H$_{42}$N$_5$O$_3$).

Example 10

Comparative $^{99m}$Tc Radiolabelling of Compound 2 vs the Corresponding Aza-Analogue (Compound 3, Prior Art)

A freeze-dried formulation containing:

23 µg Compound 2 (the benzamide derivative of Compound 1—see Example 3),

36 µg stannous chloride dihydrate,

90 µg Medronate trisodium, 4.0 mg Sodium acetate, sealed under nitrogen gas (USP/NF) in a 10 mL glass vial was prepared.

This was reconstituted with $^{99m}$Tc-pertechnetate in saline from a $^{99m}$Tc generator, at room temperature and the RCP studied by HPLC and ITLC (instant thin layer chromatography). The results were compared with those of Compound 3, and are shown in Tables 1 and 2:

TABLE 1

| ITLC radiochemical purity results (%): | | | |
|---|---|---|---|
| Time post-reconstitution (min) | Compound 3 (prior art) pH 9 | Compound 3 (prior art) pH 10 | Compound 2 pH 9 |
| 15 | 13.2 | 37.0 | 96.5 |
|  | 12.8 | 36.4 |  |
| 30 | 28.4 | 55.3 | 96.3 |
|  | 24.3 | 53.4 |  |
| 60 | 47.8 | 69.5 | 97.0 |
|  | 44.4 | 71.0 |  |
| 120 | 77.4 | 85.0 |  |
|  | 71.1 | 82.7 |  |

TABLE 2

| ITLC and HPLC radiochemical purity results for Compound 2 (%): Compound 2. | |
|---|---|
| Time post-reconstitution (min) | pH 9 |
| 15 ITLC | 95 (5% RHT) |
| 15 HPLC | 97.7 | where RHT = reduced hydrolysed technetium.

Example 11

$^{99m}$Tc Labelling of Compound 5—A Peptide Conjugate of Compound 1

A freeze-dried formulation containing:

50 µg PABA (para-aminobenzoic acid),

30 µg SnCl$_2$,

90 µg MDP (methylenediphosphonic acid), 1.32 mg NaHCO$_3$,

98 µg Na$_2$CO$_3$, 4 mg NaOAc, was sealed under nitrogen gas in a 10 ml glass vial. The vial was removed from freezer storage and left at room temperature for 15 minutes, and was then reconstituted with 100 µl of a solution containing Compound 5, ie. the peptide-chelator conjugate Ac-Asn-Gln-Glu-Gln-Val-Ser-Pro-(I-Tyr)-Thr-Leu-Leu-Lys-Gly-[Compound 1] (2 mg in 2 ml water) and Xml of $^{99m}$Tc-pertechnetate in saline, with a radioactive concentration of 0.5 GBq/ml, from an Amertec II $^{99m}$Tc generator at room temperature. The activity was measured using an ion chamber. The RCP was measured using ITLC and HPLC. The results are shown in Table 3 for different values of X:

TABLE 3

| ITLC and HPLC radiochemical purity results for Compound 5 (%): | | | | | |
|---|---|---|---|---|---|
| Prep | Reconstitution Volume X (ml) | Activity (GBq) | Time post-reconstitution (min) | RCP % (HPLC) | RCP % (ITLC) |
| 1 | 2 | 1.04 | 15 |  | 99.4 |
|  |  |  | 255 | 86.8 | 99.2 |
| 2 | 2 | 1 | 15 | 83.0 | 99.3 |
|  |  |  | 60 | 85.2 |  |
| 3 | 5 | 2.47 | 15 | 86.5 | 99.3 |
|  |  |  | 150 | 87.6 |  |
| 4 | 2 | 1.02 | 15 |  | 99.1 |
|  |  |  | 140 | 86.6 |  |

Example 12

In Vitro Clot Uptake of $^{99m}$Tc-Labelled Compound 5 vs that of $^{99m}$Tc-Labelled Compound 6 (Prior Art)

The $^{99m}$Tc radiolabelling was carried out according to Example 10. Plasma (5 ml per test article) and thrombin (100 units ml$^{-1}$) were removed from storage (−20° C.) and allowed to defrost to room temperature. Plasma was observed prior to use to ensure that there was no evidence of clot formation or sample degradation.

10 µl of $^{99m}$Tc-Compound 5 or $^{99m}$Tc-Compound 6 was added to one 5 ml vial of plasma (rat, rabbit, dog and human). 10 µl of $^{99m}$Tc-DTPA was added to a second vial containing 5 ml of plasma in parallel as a negative control. Clot forming incubation mixtures were produced by the addition of 800 µl of calcium tris buffer and 40 μl bovine thrombin solution to four vials (calcium/thrombin rich clot forming buffer). Non-clot forming incubation, the background binding assay mixtures, were produced by the addition of 800 μl tris buffered saline solution to 40 μl AnalaR water (calcium/thrombin deficient non-clot forming buffer).

400 μl of human plasma spiked with test article ($^{99m}$Tc-Compound 5 or $^{99m}$Tc-Compound 6), or radiolabelled negative control ($^{99m}$Tc-DTPA) were each added in quadruplicate to both of the calcium/thrombin rich and calcium/thrombin deficient incubation mixtures. A single defibrinating rod was added to each vial to facilitate plasma clotting. The assay vials were incubated at ambient temperature for 1 hour. The reaction was terminated by the addition of 1 ml 0.4M EDTA solution to each P7 vial.

The total radioactivity present was determined (in quadruplicate) by adding 400 μl samples of plasma previously spiked with test article and negative controls into individual glass scintillation vials. The radioactivity associated with these standards was determined by sodium iodide scintigraphy. The contents of each P7 vial was decanted onto individual BSA blocked nitrocellulose filters over a vacuum manifold. Each P7 vial was rinsed with 2 ml TBST solution. Each filter was then rinsed with four 5 ml washes of TBST solution. The clots were dried for 1 hour over the vacuum manifold. The filter papers were then transferred to individual scintillation vials, and the radioactivity present determined.

Non-specific binding of the test article to the nitrocellulose filter was factored out by subtracting the total radioactivity present in the clot forming mixture from the total radioactivity present in the non-clot forming mixture. The uptake into the clot alone (specific and non-specific) was expressed as the percentage uptake of the test article in the plasma by dividing the radioactivity present in the clot alone by the average radioactivity present in the plasma standards then multiplying by 100:

% uptake=% uptake into a clot, on a filter−% uptake on filter×100 (background corrected)

The percentage specific binding was determined as the radioactive uptake that was only due to Factor XIIIa formed isopeptide covalent bonds between fibrin and the test article. The specific binding was calculated by subtracting the background (nitrocellulose filter) corrected percentage uptake of the radiolabelled negative control ($^{99m}$Tc-DTPA) which had no affinity for FXIIIa from the background (nitrocellulose filter) corrected percentage uptake of the radiolabelled test article:

Specific binding of test article = % uptake test article − % uptake DTPA
(to clot)         (in clot)              (in clot)

Effects on In Vitro Efficacy.

The data compared the uptake of $^{99m}$Tc-Compound 5 and $^{99m}$Tc-Compound 6 into a forming plasma clot in vitro. There was no significant difference (p>0.05) in the efficacy of these two molecules (30.66±5.01 compared with 29.69±6.33) in this model of coagulation.

Example 13

$^{99m}$Tc-Labelling of Compound 9

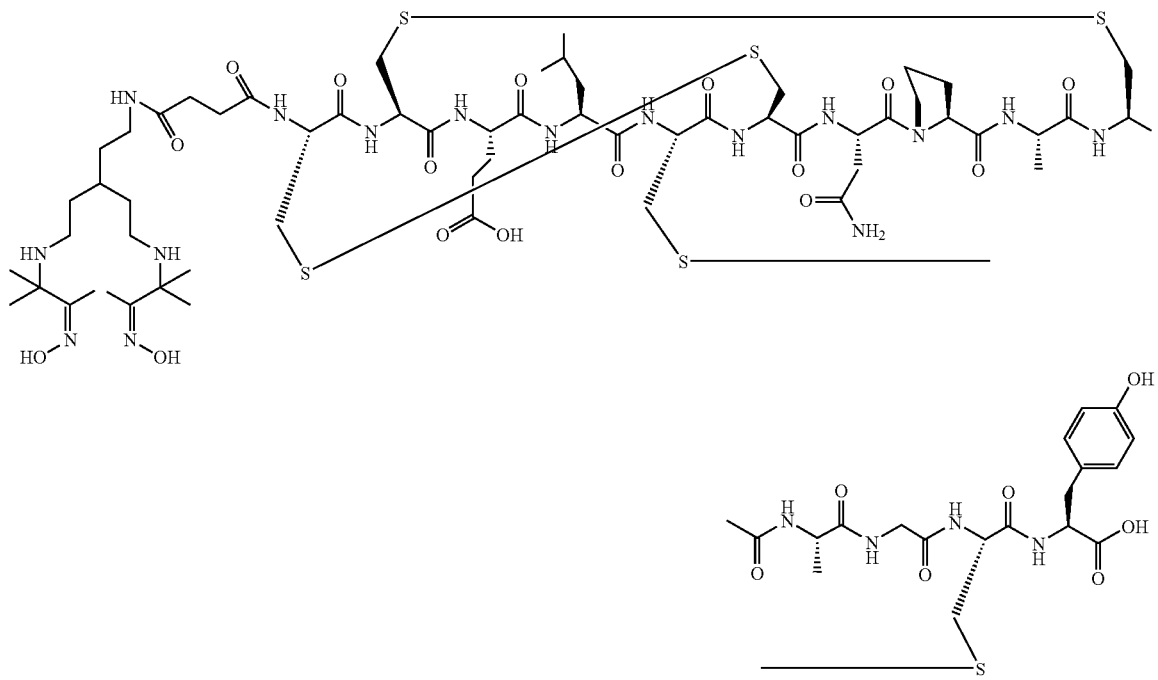

Compound 9 is the conjugate of Compound 1 with the cyclic peptide shown, ie. [Compound 1]-Cys-Cys-Glu-Leu-Cys-Cys-Asn-Pro-Ala-Cys-Ala-Cys-Tyr-OH.

Compound 9 was prepared in an analogous manner to Examples 7 and 8, and labelled with $^{99m}$Tc in solution (Preparation 1) or via a freeze-dried kit according to Example 10 (Preparation 2).

For Preparation 1, 100 μg of Compound 9 was dissolved in 1 ml of pH 8.5 borate buffer. This was transferred to a P6 vial and sealed. 1 ml $^{99m}$Tc-pertechnetate in saline (1.0 GBq/ml, from an Amertec II generator) was added at room temperature, together with 0.1 ml SnCl$_2$ solution (10 mg SnCl$_2$ in 100 ml N$_2$ purged saline). The activity was measured using an ion chamber. The RCP was measured using ITLC and HPLC.

Preparation 1 showed an RCP of 96% by ITLC, and Preparation 2 an RCP of 82% by HPLC.

The invention claimed is:

1. A chelator conjugate of formula:

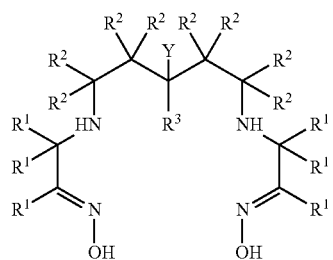

where:

each R$^1$, R$^2$ and R$^3$ is independently an R group;

Y is —CH$_2$CH$_2$—X—Z where:

X is —NR$^4$—, —CO$_2$—, —N(C=S)—, —N(C=O)—, —S— or —O—;

Z is a biological targeting moiety chosen from:
- a 3-100 mer peptide or peptide analogue which may be a linear peptide or cyclic peptide or combinations thereof;
- a monoclonal antibody or fragment thereof;
- an enzyme substrate;
- an enzyme inhibitor;
- a synthetic receptor-binding compound;
- an oligonucleotide or oligo-DNA or oligo-RNA fragment;

R$^4$ is independently an R group;

each R group is independently H or C$_{1-10}$ alkyl, C$_{3-10}$ alkylaryl, C$_{2-10}$ alkoxyalkyl, C$_{1-10}$ hydroxyalkyl, C$_{1-10}$ fluoroalkyl, or 2 or more R groups, together with the atoms to which they are attached form a carbocyclic, heterocyclic, saturated or unsaturated ring and further wherein the chelator conjugate does not encompass the formula:

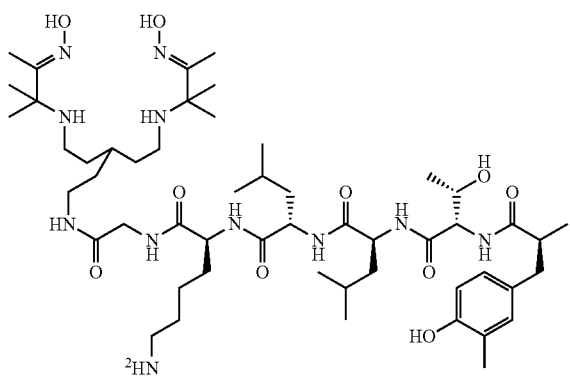

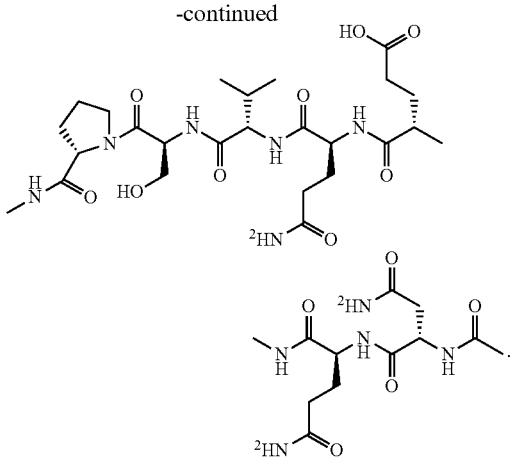

2. The chelator conjugate of claim 1, where R$^3$ is H.

3. The chelator conjugate of claim 1, where R$^2$ is H.

4. The chelator conjugate of claim 1, where X is —NR$^4$— or —CO$_2$—.

5. The chelator conjugate of claim 1, where R$^1$ is C$_{1-3}$ alkyl, C$_{2-4}$ alkoxyalkyl, C$_{1-3}$ hydroxyalkyl, or C$_{1-3}$ fluoroalkyl.

6. The chelator conjugate of claim 1, of formula:

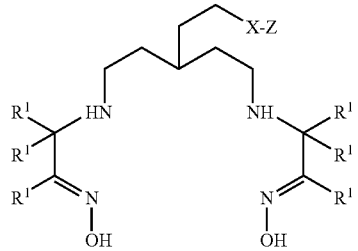

where each R$^1$ is independently C$_{1-3}$ alkyl or C$_{1-3}$ fluoroalkyl.

7. The chelator conjugate of claim 6, where the R$^1$ groups are all CH$_3$.

8. The chelator conjugate of claim 1, where Z is a 3-20 mer peptide.

9. A radiometal complex of the chelator conjugate of claim 1.

10. The radiometal complex of claim 9, where the radiometal complex is electrically neutral.

11. The radiometal complex of claim 9, where the radiometal is $^{99m}$Tc.

12. A radiopharmaceutical which comprises the radiometal complex of claim 9, in a form suitable for human administration.

13. The radiopharmaceutical of claim 12, where the radiometal is $^{99m}$Tc.

14. A kit for the preparation of the $^{99m}$Tc radiopharmaceutical of claim 13, which comprises:
  (i) the chelator conjugate of claim 1;
  (ii) a biocompatible reducing agent.

15. The kit of claim 14, where the biocompatible reducing agent is stannous.

16. A compound of formula:

[chemical structure]

where:
each $R^1$, $R^2$ and $R^3$ is independently an R group;
E is —$CH_2CH_2$-J
where:
  J is —$NR^5R^6$, —$CO_2M$, —NCS, —NCO, —$SM^1$, —$OM^1$, maleimide or acrylamide, where $R^5$ and $R^6$ are independently an R group or $P^G$; M is H, a cation, $P^G$ or an active ester; $M^1$ is H or $P^G$; and $P^G$ is a protecting group;
each R group is independently H or $C_{1-10}$ alkyl, $C_{3-10}$ alkylaryl, $C_{2-10}$ alkoxyalkyl, $C_{1-10}$ hydroxyalkyl, $C_{1-10}$ fluoroalkyl, or 2 or more R groups, together with the atoms to which they are attached form a carbocyclic, heterocyclic, saturated or unsaturated ring and further wherein the chelator conjugate does not encompass the formula:

[chemical structure]

17. The compound of claim 16, where J is —$NR^5R^6$, —$CO_2M$, —NCS, —NCO, —$SM^1$, —$OM^1$, maleimide or acrylamide, where $R^5$ and $R^6$ are independently an R group or $P^G$; M is H, a cation, $P^G$ or an active ester; $M^1$ is H or $P^G$; and $P^G$ is a protecting group.

18. The compound of claim 16, where $R^3$ is H.

19. The compound of claim 16, where each $R^2$ is H.

20. The compound of claim 16, where $R^1$ is $C_{1-3}$ alkyl, $C_{2-4}$ alkoxyalkyl, $C_{1-3}$ hydroxyalkyl, or $C_{1-3}$ fluoroalkyl.

21. The compound of claim 16 where J is —$NHR^5$ and $R^5$ is H or $C_{1-3}$ alkyl.

22. The compound:

[chemical structure]

23. A compound of formula:

$$HC(CH^2CH_2NR^7R^8)_3,$$

where $R^7$ and $R^8$ are independently H or $P^G$, or $R^7$ and $R^8$ together form $P^G$;
wherein $P^G$ is a protecting group chosen from tert-butyloxycarbonyl, fluorenylmethoxycarbonyl, trifluoroacetyl, allyloxycarbonyl, 1-(4,4-dimethyl-2,6-dioxocyclohexylidene)ethyl or 3-nitro-2-pyridine sulfenyl;
or a salt thereof;
wherein at least one of $R^7$ or $R^8$ is $P^G$.

24. A process for the preparation of the compound of claim 16, which comprises alkylation of a compound of Formula IV:

[chemical structure] Formula IV with either:
(i) a chloronitroso compound of formula Cl—$C(R^1)_2$—CH(NO)$R^1$; or
(ii) an alpha-chloro oxime of formula Cl—$C(R^1)_2$—C(=NOH)$R^1$; or (iii) an alpha-bromoketone of formula Br—C($R^1$)$_2$—C(=O)$R^1$ followed by conversion of the diaminediketone product to the diaminedioxime with hydroxylamine;

where A, J, $R^1$, $R^2$, $R^3$ and n are as defined in claim 16.

25. A process for the preparation of the compound of claim 22, which comprises alkylation of HC(CH$_2$CH$_2$NH$_2$)$_3$ with either:
(i) a chloronitroso derivative of formula Cl—C(CH$_3$)$_2$—CH(NO)CH$_3$; or
(ii) an alpha-chloro oxime of formula Cl—C(CH$_3$)$_2$—C(=NOH)CH$_3$; or
(iii) an alpha-bromoketone of formula Br—C(CH$_3$)$_2$—C(=O)CH$_3$ followed by conversion of the diaminediketone product to the diaminedioxime with hydroxylamine.

* * * * *